(12) United States Patent
Hultsch et al.

(10) Patent No.: US 9,000,037 B2
(45) Date of Patent: Apr. 7, 2015

(54) PRECURSORS OF GLUTAMATE DERIVATIVES

(75) Inventors: Christina Hultsch, Berlin (DE); Michael Harre, Berlin (DE); Filip Novak, Berlin (DE); Mathias Berndt, Berlin (DE); Matthias Friebe, Berlin (DE); Heribert Schmitt-Willich, Berlin (DE); Dae Yoon Chi, Seoul (KR); Byoung Se Lee, Incheon (KR); Sang Don Park, Seoul (KR)

(73) Assignee: Piramal Imaging SA, Matran (CH)

( * ) Notice: Subject to any disclaimer, the term of this patent is extended or adjusted under 35 U.S.C. 154(b) by 0 days.

(21) Appl. No.: 14/115,127

(22) PCT Filed: Apr. 30, 2012

(86) PCT No.: PCT/EP2012/057884
§ 371 (c)(1),
(2), (4) Date: May 15, 2014

(87) PCT Pub. No.: WO2012/150204
PCT Pub. Date: Nov. 8, 2012

(65) Prior Publication Data
US 2014/0243532 A1      Aug. 28, 2014

(30) Foreign Application Priority Data

May 3, 2011    (EP) .................................... 11075077

(51) Int. Cl.
| | | |
|---|---|---|
| *A61K 31/04* | (2006.01) |
| *C07C 309/77* | (2006.01) |
| *C07B 59/00* | (2006.01) |
| *C07C 227/16* | (2006.01) |
| *C07C 227/18* | (2006.01) |
| *C07C 229/24* | (2006.01) |
| *C07C 309/73* | (2006.01) |
| *C07C 309/74* | (2006.01) |
| *C07D 215/36* | (2006.01) |
| *C07C 229/36* | (2006.01) |
| *C07C 303/28* | (2006.01) |

(52) U.S. Cl.
CPC ............. *C07C 309/77* (2013.01); *C07B 59/001* (2013.01); *C07C 227/16* (2013.01); *C07C 227/18* (2013.01); *C07C 229/24* (2013.01); *C07C 309/73* (2013.01); *C07C 309/74* (2013.01); *C07D 215/36* (2013.01); *C07C 229/36* (2013.01); *C07C 303/28* (2013.01); *C07B 2200/05* (2013.01)

(58) Field of Classification Search
USPC .............. 558/48; 546/153; 514/312, 517, 547
See application file for complete search history.

(56) References Cited

U.S. PATENT DOCUMENTS

2011/0064673 A1    3/2011    Dinkelborg et al.
2011/0137063 A1    6/2011    Srinivasan et al.

FOREIGN PATENT DOCUMENTS

| WO | 2008/052788 | * | 5/2008 |
| WO | 2009/141090 A1 | | 11/2009 |
| WO | 2010/000409 A2 | | 1/2010 |

OTHER PUBLICATIONS

International Search Report dated Jul. 9, 2012 issued in corresponding PCT/EP2012/057884 application (pp. 1-3).

* cited by examiner

*Primary Examiner* — D M Seaman
(74) *Attorney, Agent, or Firm* — Millen, White, Zelano & Branigan, P.C.

(57) ABSTRACT

This invention relates to novel precursors suitable for $^{18}F$ radiolabeling of glutamate derivatives, methods for preparing such compounds and its intermediates, compositions comprising such compounds, kits comprising such compounds or compositions and methods for $^{18}F$ radiolabeling of glutamate derivatives wherein the obtained $^{18}F$ radiolabeled glutamate derivatives are suitable for diagnostic imaging by Positron Emission Tomography (PET) of proliferative diseases e.g. tumor in mammals.

9 Claims, No Drawings

US 9,000,037 B2

PRECURSORS OF GLUTAMATE DERIVATIVES

FIELD OF INVENTION

This invention relates to novel precursors suitable for $^{18}$F radiolabeling of glutamate derivatives, methods for preparing such compounds and their intermediates, compositions comprising such compounds, kits comprising such compounds or compositions and methods for $^{18}$F radiolabeling of glutamate derivatives wherein the obtained $^{18}$F radiolabeled glutamate derivatives are suitable for diagnostic imaging by Positron Emission Tomography (PET) of proliferative diseases e.g. tumor in mammals.

BACKGROUND

The early diagnosis of malignant tumor diseases plays an important role in the survival prognosis of a tumor patient. For this diagnosis, non-invasive diagnostic imaging methods are an important aid. In the last years, in particular the PET (Positron Emission Tomography) technology has been found to be particularly useful. The sensitivity and specificity of the PET technology depends essentially on the signal-giving substance (tracer) used and on its distribution in the body. In the hunt for suitable traces, one tries to make use of certain properties of tumors which differentiate tumor tissue from healthy surrounding tissue. The preferred commercial isotope used for PET applications is $^{18}$F. Owing to the short half-life of less than 2 hours, $^{18}$F is particularly demanding when it comes to the preparation of suitable tracers. This isotope does not allow complicated long synthesis routes and purification procedures, since otherwise a considerable amount of the radioactivity of the isotope will already have decayed before the tracer can be used for diagnosis. Therefore, often it is not possible to apply established synthesis routes for non-radioactive fluorinations to the synthesis of $^{18}$F tracers. Furthermore, the high specific activity of $^{18}$F (about 80 GBq/nmol) leads to very low substance amounts of [$^{18}$F] fluoride for the tracer synthesis, which in turn requires an extreme excess of precursor, making the result of a radio synthesis strategy based on a non-radioactive fluorination reaction unpredictable.

FDG ([$^{18}$F]-2-Fluorodeoxyglucose)-PET is a widely accepted and frequently used auxiliary in the diagnosis and further clinical monitoring of tumor disorders. Malignant tumors compete with the host organism for glucose as nutrient supply (Warburg O., Über den Stoffwechsel der Carcinomzelle [The metabolism of the carcinoma cell], *Biochem. Zeitschrift* 1924; 152: 309-339; Kellof G., Progress and Promise of FDG-PET Imaging for Cancer Patient Management and Oncologic Drug Development, *Clin. Cancer Res.* 2005; 11(8): 2785-2807). Compared to the surrounding cells of the normal tissue, tumor cells usually have an increased glucose metabolism. This is exploited when using fluorodeoxyglucose (FDG), a glucose derivative which is increasingly transported into the cells, where, however, it is metabolically captured as FDG 6-phosphate after phosphorylation ("Warburg effect"). Accordingly, $^{18}$F-labeled FDG is an effective tracer for detecting tumor disorders in patients using the PET technology. In the hunt for novel PET tracers, recently, amino acids have been employed increasingly for $^{18}$F PET imaging (for example (review): *Eur. J. Nucl. Med. Mol. Imaging.* May 2002; 29(5): 681-90). Here, some of the $^{18}$F-labeled amino acids are suitable for measuring the rate of protein synthesis, but most other derivatives are suitable for measuring the direct cellular uptake in the tumor. Known $^{18}$F-labeled amino acids are derived, for example, from tyrosine amino acids, phenylalanine amino acids, proline amino acids, asparagine amino acids and unnatural amino acids (for example *J. Nucl. Med.* 1991; 32: 1338-1346, *J. Nucl. Med.* 1996; 37: 320-325, *J. Nucl. Med.* 2001; 42: 752-754 and *J. Nucl. Med.* 1999; 40: 331-338).

Recently, the use and the synthesis of $^{18}$F/$^{19}$F-labeled glutamic acid derivatives and glutamine derivatives has been published (WO2008052788, WO2009141091). Compounds with very promising preclinical results (WO2008052788, J. Med. Chem. 2011; (54):406-410, J Nucl Med. 2010; 51 (Supplement 2):1535) were tested in first clinical studies. For [$^{18}$F]-4-fluoro-glutamic acid good tumor uptake was found. However, some defluorination was detected which negatively influenced the tumor-background-ratio. (J Nucl Med. 2010; 51 (Supplement 2):118). Superior results were obtained applying (S)-4-(3-[$^{18}$F]Fluoropropyl)-L-glutamic acid in first clinical studies. Very good results were found in the detection of lung cancer (Koglin et al., Abstract Nr. 412, SNM 2011, San Antonio; Baek et al., Abstract Nr. 195, SNM 2011, San Antonio).

Common leaving groups for labeling in alkyl positions described in the literature are sulfonates such as mesylate, tosylate, and triflate or halides (Ernst Schering Res Found Workshop. 2007; (62):15-50 and Eur. J. Org. Chem. 2008, 2853-2873).

Novel leaving groups with different scopes have been published. Lu et al. describe the use of leaving groups which already contain the phase transfer catalyst for the introduction of the [$^{18}$F]fluoride (Lu et al. J. Org. Chem. 2009; (74):5290-5296). These leaving groups contain an arylsulfonate and a chelating unit which is attached to the aryl ring via an ether ring.

Furthermore, the use of special leaving groups which support the removal of the precursor in a purification step after the radiolabeling was reported (WO2011006610). The leaving groups described are sulfonates containing a lipophilic part to allow a simple purification.

For the synthesis of 4-(3-[$^{18}$F]Fluoropropyl)-L-glutamic acid different precursors have been described.

In WO2008052788 and WO2009141091, the precursor is a combination of known amino and carboxyl protecting groups and leaving groups such as of Chloro, Bromo, sulfonate derivatives such as Tosyloxy resulting into a suitable $^{18}$F radiolabeling precursor in oily form. WO2010000409 refers to the use of novel perfluorinated precursors, its $^{18}$F-radiolabeling and the purification of the resulting compound. These methods were also applied for the manufacture of 4-(3-[$^{18}$F] Fluoropropyl)-L-glutamic acid.

However, the synthesis of the compound remains challenging. One important factor in the production of the radiotracer is a precursor suitable for $^{18}$F radiolabeling. Due to the presence of different functional groups (carboxylic group, amino group) the introduction of protecting groups is necessary for conducting the radiolabeling without loss of functional groups. In addition, the presence of a leaving group is required to enable the nucleophilic introduction of the $^{18}$F-label.

Until now, no solid precursor for the synthesis of 4-(3-[$^{18}$F] Fluoropropyl)-L-glutamic acid has been described.

PROBLEM TO BE SOLVED BY THE INVENTION AND ITS SOLUTION

For a routine clinical use of a 4-(3-[$^{18}$F]Fluoropropyl)-L-glutamic acid, a reliable and robust manufacturing process is needed, that is compliant with Good Manufacturing Practice requirements (GMP) and provides a stable injectable solution (isotonic, appropriate pH) of the radiotracer with a low content of impurities.

In face of the short half-live of $^{18}$F (110 min), the process has to provide the radiolabeled tracer in high radiochemical yield within short synthesis time (preferably less than 60 min). Manufacturing of the radiolabeled tracer is usually performed on automated systems. For routine applications pre-manufactured Kits containing (inter alia) the required amount of precursor are frequently used. In general, the reagents used for the manufacture of the radiolabeled tracer—including the precursor—need sufficient stability for shipment and storage.

Furthermore, the physicochemical nature of the precursor is also very important: oily or resinous precursors cause technical problems during filling (e.g. into Kits). Either the weighing of an accurate precursor amount is tedious and expensive or the weighed amount is not exact. The latter can cause synthetic problems or result in higher impurity content. It is therefore preferable to have solid precursors.

The glutamic acid derivatives of the present invention of formula Ia and IIa, as well as Ib and IIb have two stereo centers in the 2 and 4 positions. A method for manufacturing these compounds has to ensure high optical purity.

$^{18}$F labeled glutamic acid derivatives of formula IIIa-F18 and IVa-F18, as well as IIIb-F18 and IVb-F18 have also two stereo centers in the 2 and 4 positions. A method for manufacturing these compounds has to assure, that the labeling reaction conditions do not lead to a significant degree of epimerization at one or both stereo centers.

For the manufacture of (S)-4-(3-[$^{18}$F]Fluoropropyl)-L-glutamic acid or for (R)-4-(3-[$^{18}$F]-Fluoropropyl)-L-glutamic acid it is therefore desirable to have a precursor that is:
1. stable
2. solid and
3. labeled under sufficiently mild conditions, preventing the loss of stereochemical integrity.

The present invention solves the above mentioned problems by providing stable (e.g. storage at ≥−20° C.), optically pure, solid and sufficiently reactive precursors for the manufacturing of fluorine labeled glutamate derivatives.

Remotely controlled synthesizers for $^{18}$F labeling are adaptable to these precursors to allow a GMP compliant manufacturing of the radio tracer.

SUMMARY OF THE INVENTION

For the synthesis of (S)-4-(3-[$^{18}$F]Fluoropropyl)-L-glutamic acid new stable and solid labeling precursors of Formula Ia have been invented. The problems mentioned above have been solved by the introduction of a special combination of the protecting groups and the leaving groups. Especially, the use of a trityl protecting group at the amino function in combination with an aromatic ring containing leaving group resulted in solid compounds. The resulting precursors can be easily $^{18}$F-radiolabeled and deprotected to obtain (S)-4-(3-[$^{18}$F]-Fluoropropyl)-L-glutamic acid (scheme 1a). The new precursors of Formula Ib bearing the substituent at C-4 in "R" orientation can be used for the manufacturing of (R)-4-(3-[$^{18}$F]-Fluoropropyl)-L-glutamic acid (scheme 1b).

Scheme 1a: Synthesis of (S)-4-(3-[$^{18}$F]Fluoropropyl)-L-glutamic acid (IVa-F18) from compounds of Formula Ia.

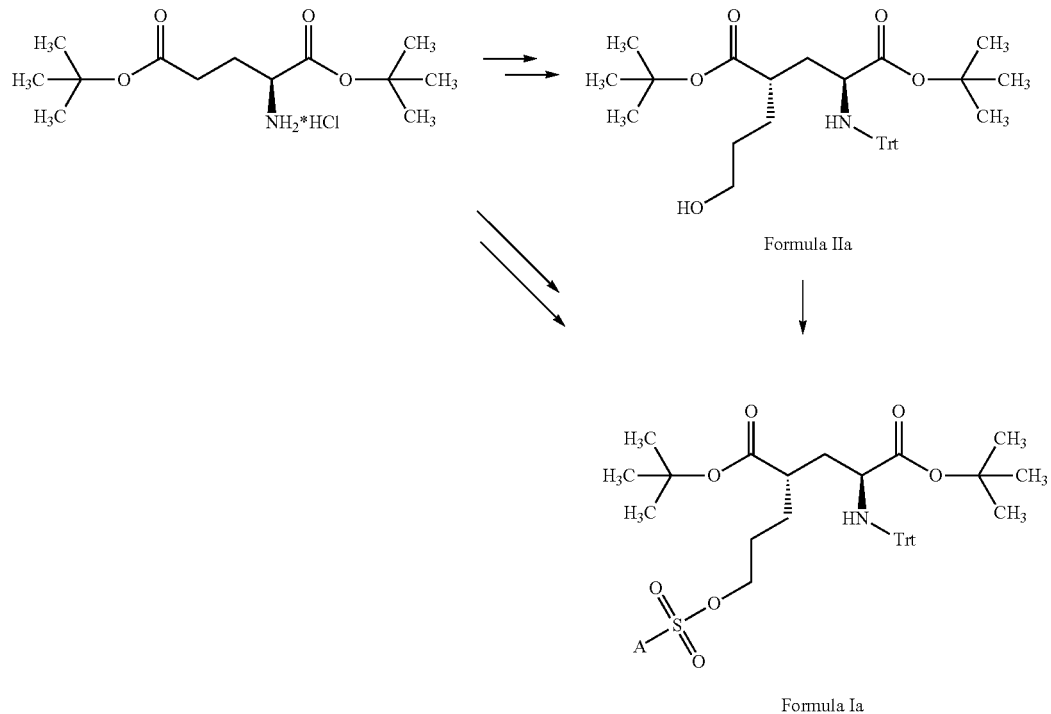

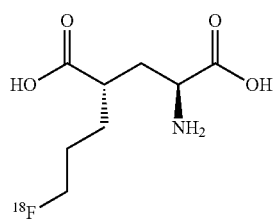
Formula IVa-F18
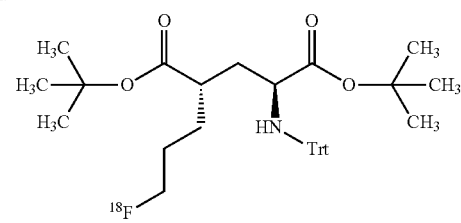
Formula IIIa-F18
Scheme 1b: Synthesis of (R)-4-(3-[$^{18}$F]Fluoropropyl)-L-glutamic acid (IVb-F18) from compounds of Formula Ib.
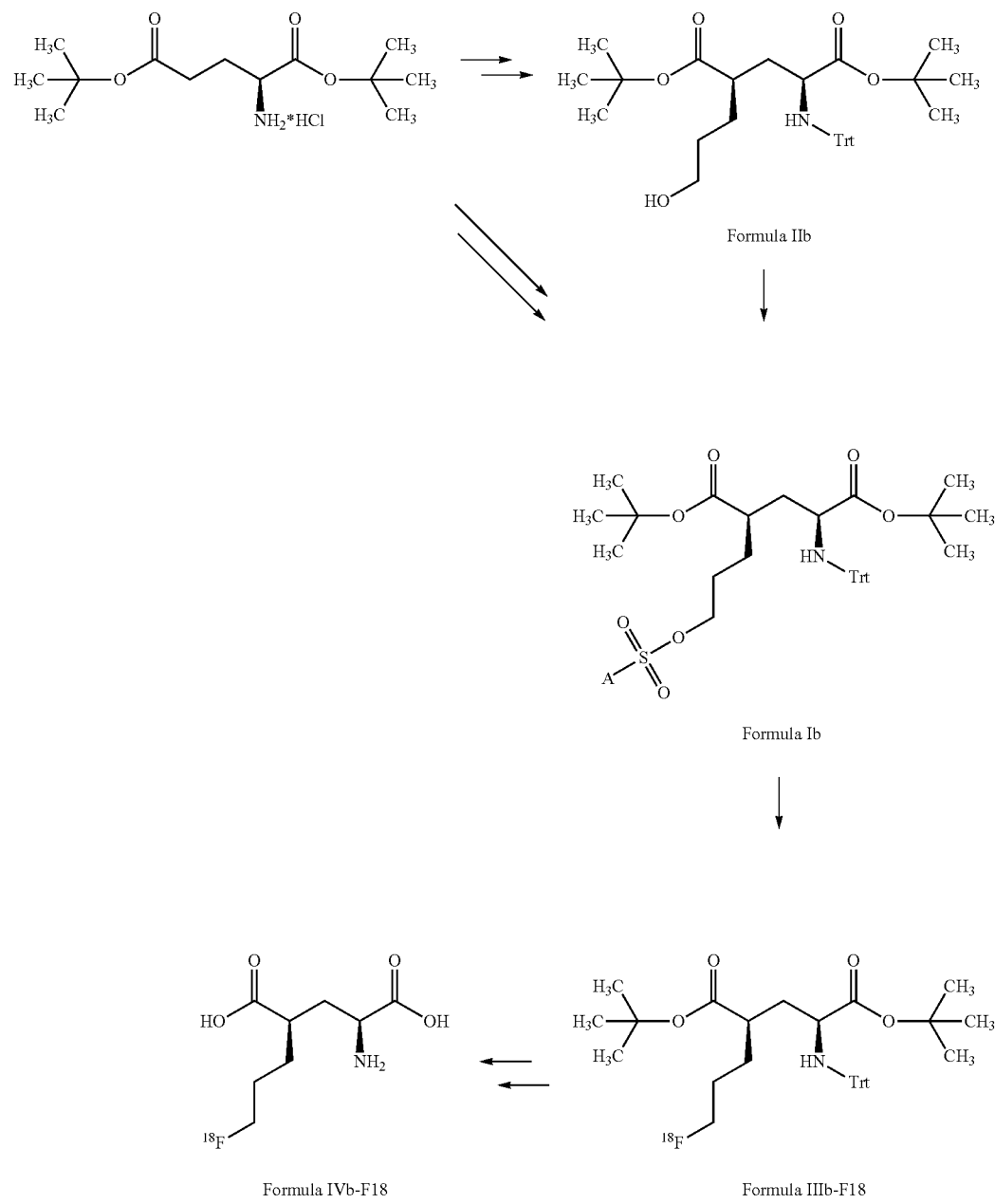

The present invention provides furthermore methods for manufacturing of radiolabeled compounds of Formula IV-F18, IVa-F18 and IVb-F18 using herein disclosed compounds of Formula I, Ia and Ib.

DETAILED DESCRIPTION OF THE INVENTION

In a first aspect, the invention is directed to compounds of the formula I (precursors), Formula I

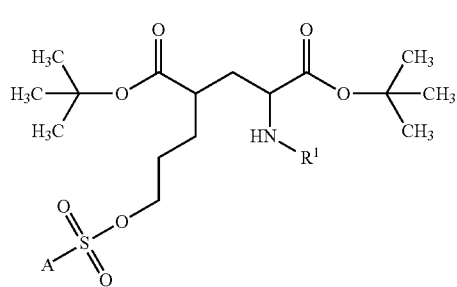

wherein
R¹ is triphenylmethyl (Trityl),
A is selected from the group:
a) Monocyclic aryl,
b) Bicyclic aryl,
c) Biaryl,
d) Monocyclic heteroaryl, and
e) Bicyclic heteroaryl
optionally, A is bearing one or more substituents selected from the group comprising:
a) Halogen,
b) Nitro,
c) Alkyl,
d) Trifluoromethyl, and
e) Z,
wherein Z is

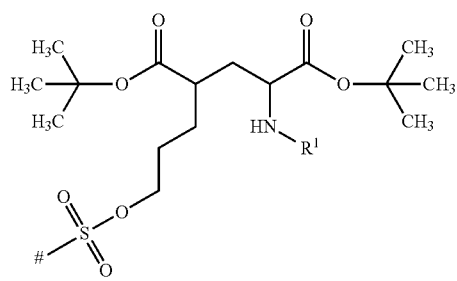

R¹ is triphenylmethyl (Trityl),
# indicates the position of the bond to A, and
single isomers, tautomers, diastereomers, enantiomers, stereoisomers, mixtures thereof, and suitable salts thereof.
Preferred Features:
Preferably, A is selected from the group:
a) phenyl,
b) biphenyl,
c) naphthyl, and
d) quinolinyl,
optionally, A is bearing 1 to 4 substituents selected from the group comprising:
a) Halogen,
b) Nitro,
c) $C_1$-$C_3$ alkyl,
d) Trifluoromethyl, and
e) Z.
More preferably, A is selected from the group:
a) phenyl,
b) biphenyl,
c) naphthyl, and
d) quinolinyl,
optionally, A is bearing 1 to 3 substituents selected from the group comprising:
a) Halogen,
b) Nitro,
c) Trifluoromethyl, and
d) Z.
Even more preferably, A is selected from the group:
a) phenyl,
b) biphenyl,
c) naphthyl, and
d) quinolinyl,
optionally, A is bearing 1 to 3 substituents selected from the group comprising:
a) Chloro,
b) Nitro,
c) Trifluoromethyl, and
d) Z.
Even more preferably, A is selected from the group:
a) phenyl,
b) biphenyl,
c) naphthyl, and
d) quinolinyl,
optionally, A is bearing 1 to 3 substituents selected from the group comprising:
a) Chloro,
b) Nitro, and
c) Trifluoromethyl.
Even more preferably, A is selected from the group:
a) phenyl,
b) biphenyl,
c) naphthyl, and
d) quinolinyl,
optionally, A is bearing 1 to 3 substituents selected from Chloro, and
optionally, A is bearing 1 substituent selected from the group consisting of:
a) Nitro, and
b) Trifluoromethyl.
In a preferred embodiment A is phenyl, optionally substituted as described above.
In another preferred embodiment A is biphenyl, optionally substituted as described above.
In another preferred embodiment A is naphthyl, optionally substituted as described above.
In another preferred embodiment A is quinolinyl, optionally substituted as described above.
In a more preferred embodiment A is nitrophenyl.
In another more preferred embodiment A is biphenyl.
In another more preferred embodiment A is quinolinyl.
In another more preferred embodiment A is biphenyl-Z.
In a more preferred embodiment A is nitro-(trifluoromethy)phenyl.
In a more preferred embodiment A is naphthyl.
In a more preferred embodiment A is trichlorophenyl.
In a more preferred embodiment A is nitronaphthyl.

In an even more preferred embodiment A is

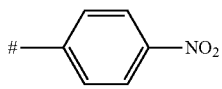

In another even more preferred embodiment A is

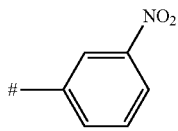

In another even more preferred embodiment A is

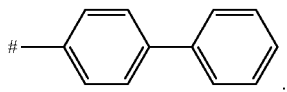

In another even more preferred embodiment A is

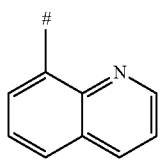

In another even more preferred embodiment A is

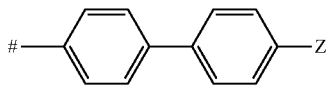

In another even more preferred embodiment A is

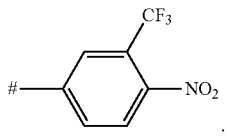

In another even more preferred embodiment A is

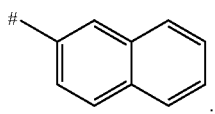

In another even more preferred embodiment A is

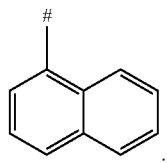

In another even more preferred embodiment A is

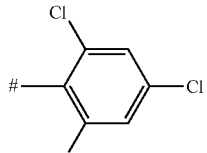

In another even more preferred embodiment A is

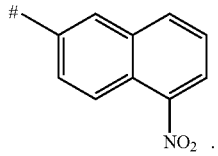

In another even more preferred embodiment A is

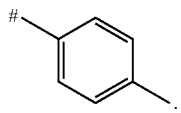

# indicates the position of the bond to A in formula I.

Halogen is Chloro, Fluoro, Iodo or Bromo. Preferably, halogen is Chloro.

Alkyl is a branched or unbranched $C_1$-$C_6$ Alkyl. Preferably, alkyl is methyl, ethyl or propyl.

In a preferred embodiment formula I relates to compounds with (2S,4S)-configuration (compound of formula Ia) with diastereomeric and enantiomeric purity of >80%, preferably >90%, more preferably 95% and even more preferably >98%.

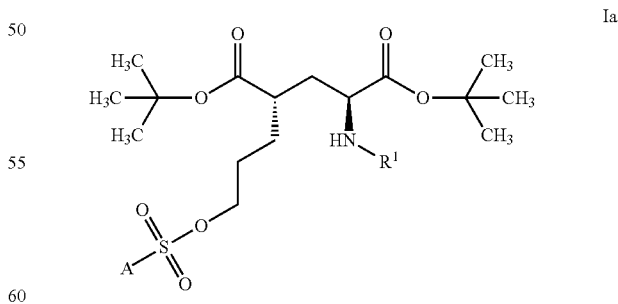

Ia wherein A and $R^1$ are defined as for formula I above.

In another preferred embodiment formula I relates to compounds with (2S,4R)-configuration (compound of formula Ib) with diastereomeric and enantiomeric purity of >80%, preferably >90%, more preferably 95% and even more preferably >98%.

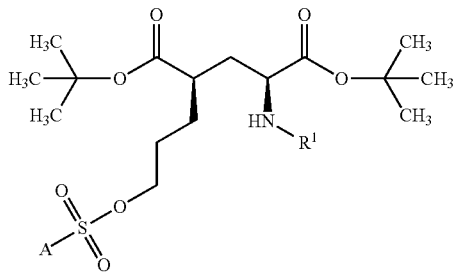

wherein A and R¹ are defined as for formula I above.

A preferred compound of Formula I is di-tert-butyl (4S)-4-(3-{[(4-nitrophenyl)sulfonyl]oxy}propyl)-N-trityl-L-glutamate

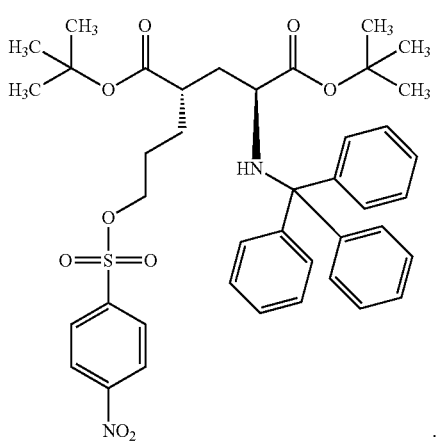 [SMILES: CC(C)(C)OC(=O)[C@@H](CCCOS(=O)(=O)c1ccc([N+](=O)[O-])cc1)C[C@H](NC(c1ccccc1)(c1ccccc1)c1ccccc1)C(=O)OC(C)(C)C]

A preferred compound of Formula I is di-tert-butyl (4S)-4-(3-{[(3-nitrophenyl)sulfonyl]oxy}propyl)-N-trityl-L-glutamate

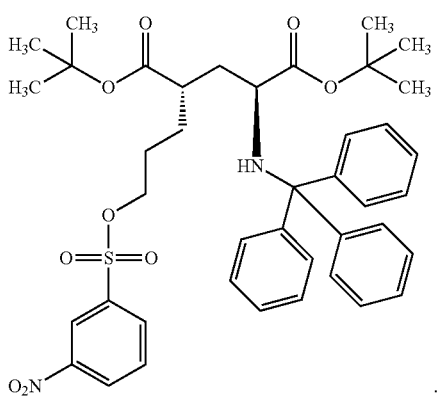 [SMILES: CC(C)(C)OC(=O)[C@@H](CCCOS(=O)(=O)c1cccc([N+](=O)[O-])c1)C[C@H](NC(c1ccccc1)(c1ccccc1)c1ccccc1)C(=O)OC(C)(C)C]

A preferred compound of Formula I is di-tert-butyl (4S)-4-{3-[(biphenyl-4-ylsulfonyl)oxy]propyl}-N-trityl-L-glutamate

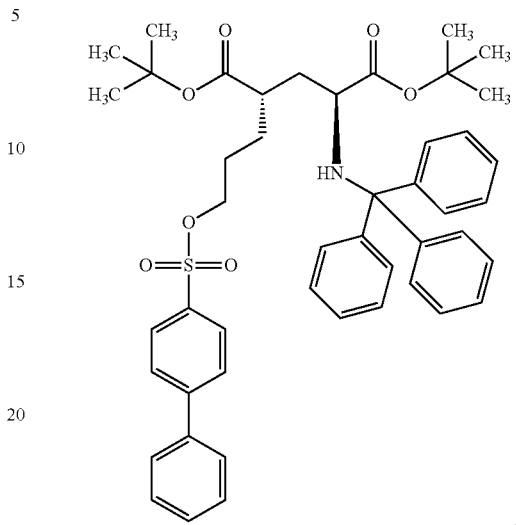

A preferred compound of Formula I is di-tert-butyl (4S)-4-{3-[(2-naphthylsulfonyl)oxy]propyl}-N-trityl-L-glutamate

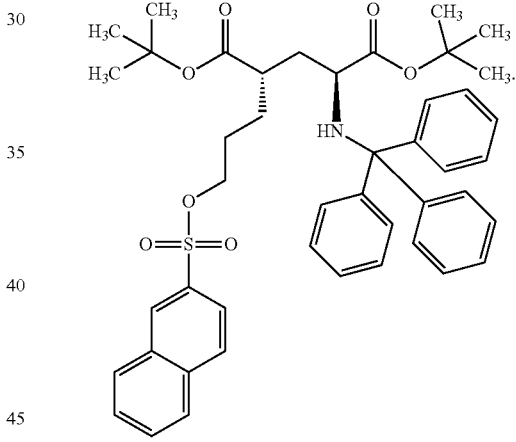

A preferred compound of Formula I is di-tert-butyl (4S)-4-{3-[(1-naphthylsulfonyl)oxy]propyl}-N-trityl-L-glutamate

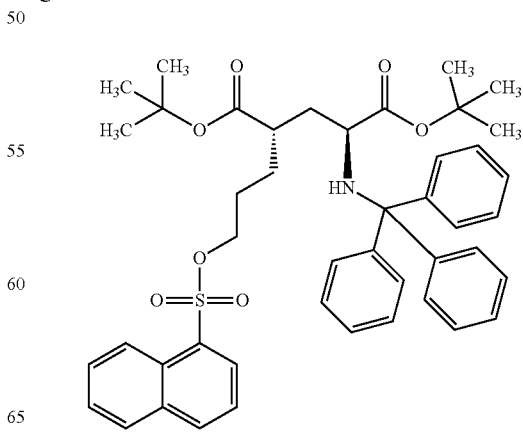

A preferred compound of Formula I is di-tert-butyl (4S)-4-{3-[(quinolin-8-ylsulfonyl)oxy]propyl}-N-trityl-L-glutamate

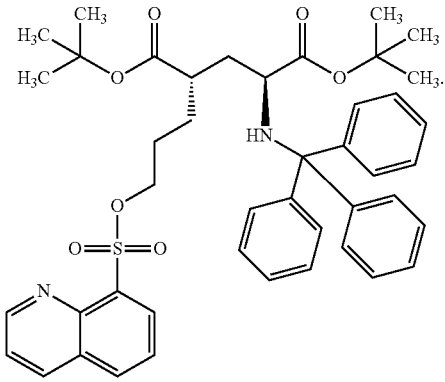 [SMILES: CC(C)(C)OC(=O)[C@@H](CCCOS(=O)(=O)c1cccc2cccnc12)C[C@H](NC(c1ccccc1)(c1ccccc1)c1ccccc1)C(=O)OC(C)(C)C]

A preferred compound of Formula I is di-tert-butyl (4S)-4-(3-{[(2,4,6-trichlorophenyl)sulfonyl]oxy}propyl)-N-trityl-L-glutamate

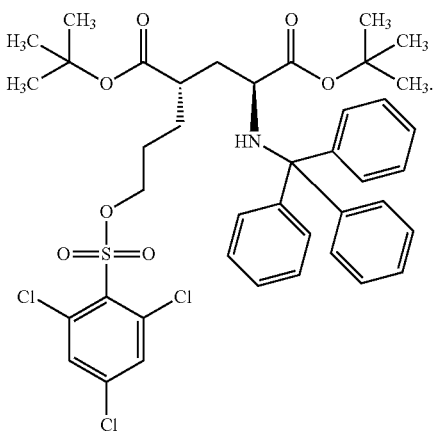 [SMILES: CC(C)(C)OC(=O)[C@@H](CCCOS(=O)(=O)c1c(Cl)cc(Cl)cc1Cl)C[C@H](NC(c1ccccc1)(c1ccccc1)c1ccccc1)C(=O)OC(C)(C)C]

A preferred compound of Formula I is tetra-tert-butyl (2S,4S,2'S,4'S)-2,2'-[biphenyl-4,4'-diylbis(sulfonyloxypropane-3,1-diyl)]bis[4-(tritylamino)pentanedioate]

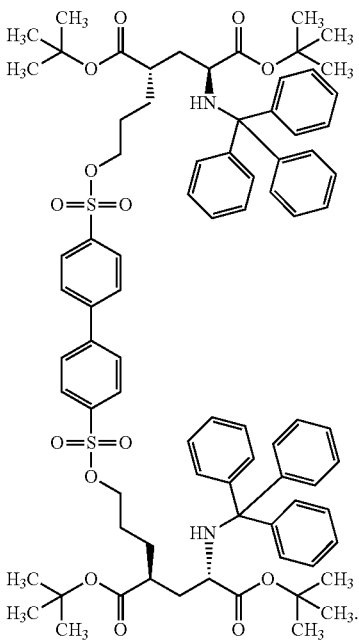 [SMILES: CC(C)(C)OC(=O)[C@@H](CCCOS(=O)(=O)c1ccc(-c2ccc(S(=O)(=O)OCCC[C@@H](C[C@H](NC(c3ccccc3)(c3ccccc3)c3ccccc3)C(=O)OC(C)(C)C)C(=O)OC(C)(C)C)cc2)cc1)C[C@H](NC(c1ccccc1)(c1ccccc1)c1ccccc1)C(=O)OC(C)(C)C]

A preferred compound of Formula I is di-tert-butyl (4S)-4-(3-{[(7-nitro-1-naphthyl)sulfonyl]oxy}propyl)-N-trityl-L-glutamate

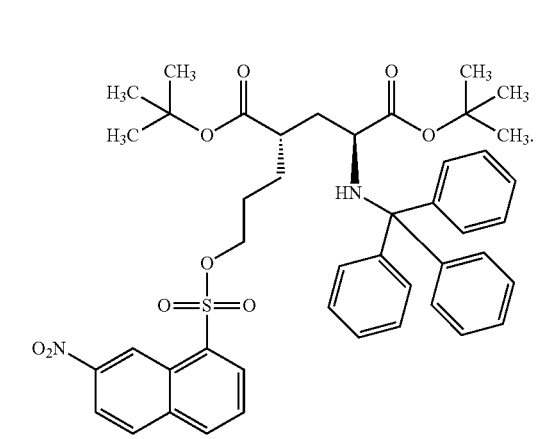 [SMILES: CC(C)(C)OC(=O)[C@@H](CCCOS(=O)(=O)c1cccc2ccc([N+](=O)[O-])cc12)C[C@H](NC(c1ccccc1)(c1ccccc1)c1ccccc1)C(=O)OC(C)(C)C]

A preferred compound of Formula I is di-tert-butyl (4S)-4-[3-({[4-nitro-3-(trifluoromethyl)phenyl]sulfonyl}oxy)propyl]-N-trityl-L-glutamate

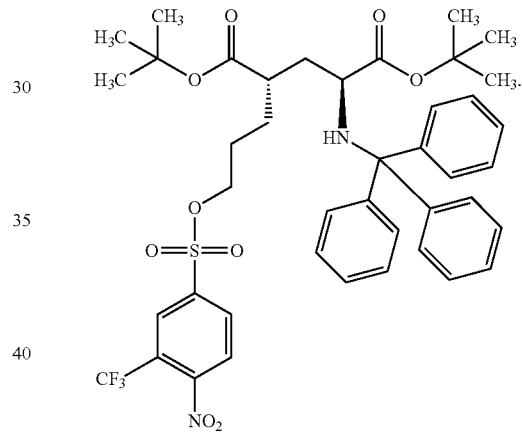

A preferred compound of Formula I is di-tert-butyl (4S)-4-(3-{[(4-methylphenyl)sulfonyl]oxy}propyl)-N-trityl-L-glutamate.

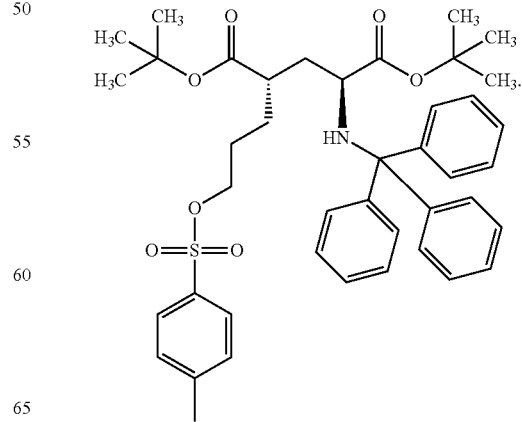

A preferred compound of Formula I is di-tert-butyl (4R)-4-(3-{[(4-methylphenyl)sulfonyl]oxy}propyl)-N-trityl-L-glutamate.

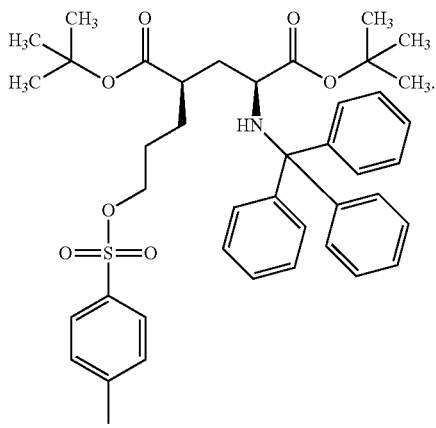 [SMILES: Cc1ccc(S(=O)(=O)OCCC[C@H](C[C@H](NC(c2ccccc2)(c2ccccc2)c2ccccc2)C(=O)OC(C)(C)C)C(=O)OC(C)(C)C)cc1]

A preferred compound of Formula I is di-tert-butyl (4R)-4-{3-[(2-naphthylsulfonyl)oxy]propyl}-N-trityl-L-glutamate

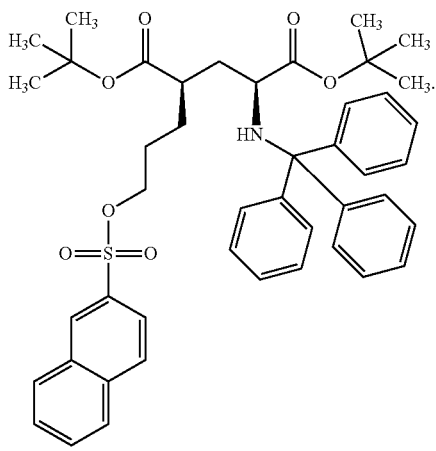 [SMILES: CC(C)(C)OC(=O)[C@H](CCCOS(=O)(=O)c1ccc2ccccc2c1)C[C@H](NC(c1ccccc1)(c1ccccc1)c1ccccc1)C(=O)OC(C)(C)C]

The second aspect of the present invention is directed to compounds of Formula I, Ia or Ib in the solid form. Preferably, the present invention is directed to the solid compounds of Formula I, Ia or Ib as listed above.

Additionally the invention is directed to methods for obtaining a crystalline form of compounds of formula I, Ia or Ib. Crystallization methods are well known to the person skilled in is the art.

In a preferred embodiment, the present invention is directed to crystalline compounds of Formula I, Ia or Ib.

Preferably, the following compound is in a crystalline form Di-tert-butyl (4S)-4-{3-[(2-naphthylsulfonyl)oxy]propyl}-N-trityl-L-glutamate.

Preferably, the following compound is in a crystalline form Di-tert-butyl (4R)-4-{3-[(2-naphthylsulfonyl)oxy]propyl}-N-trityl-L-glutamate.

In a third aspect, the invention is directed to methods for obtaining compounds of formula I.

Method for Obtaining Compounds of Formula I

The method for obtaining compounds of formula I is performed by sulfonylation of the hydroxy group in Formula II with a suitable sulfonylhalide (preferably, sulfonylchloride) or anhydride with a suitable substituent A to form a compound of formula I as defined above. The method for obtaining compounds of formula I comprises the step:

Sulfonylation of compound of Formula II with a sulfonylhalide (preferably, sulfonylchloride) or sulfonyl anhydride having both a suitable substituent A.

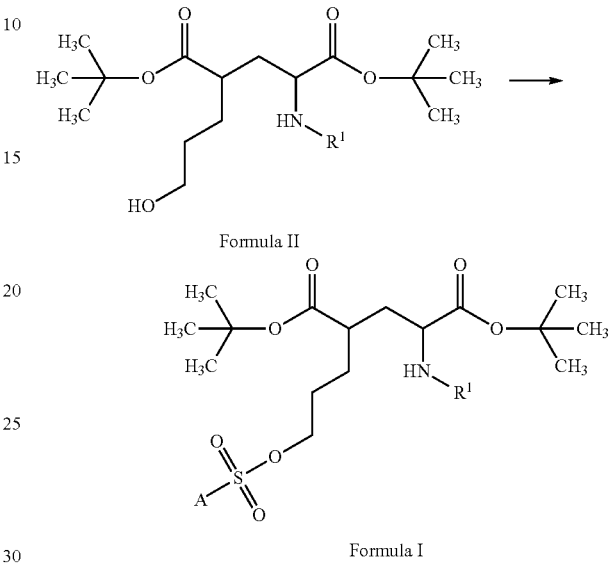

wherein $R^1$ is triphenylmethyl (Trityl),
A is selected from the group:
a) Monocyclic aryl,
b) Bicyclic aryl,
c) Biaryl,
d) Monocyclic heteroaryl, and
e) Bicyclic heteroaryl
optionally, A is bearing one or more substituents selected from the group comprising:
a) Halogen,
b) Nitro,
c) Alkyl,
d) Trifluoromethyl, and
e) Z,
Z is

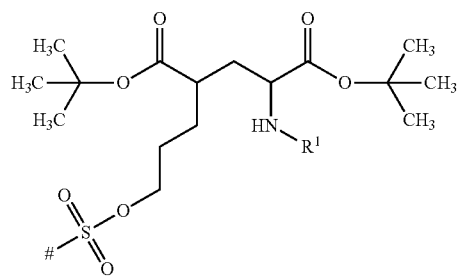

$R^1$ is triphenylmethyl (Trityl),
# indicates the position of the bond to A.

In another embodiment, a bis-sulfonylhalide X—$SO_2$-A-$SO_2$—X is reacted with two molecules of compound of formula II to obtain a compound of formula I, wherein A is substituted with Z as describe above. X is halogen, preferably X is Chloro.

Method for Obtaining Compounds of Formula Ia

Preferably, the method is conducted by reacting compounds of formula IIa for obtaining compounds of formula Ia with (2S,4S)-configuration Sulfonylation of compound of Formula IIa with a sulfonylhalide (preferably, sulfonylchloride) or sulfonyl anhydride having both a suitable substituent A.

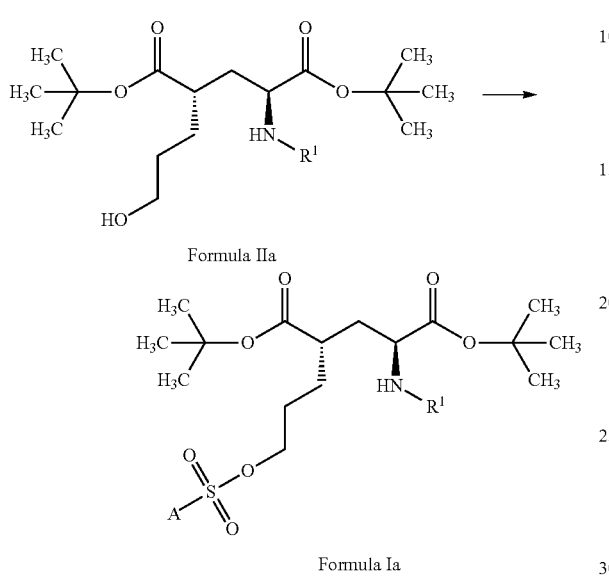

Formula IIa

Formula Ia wherein A and R¹ are defined above.

Method for Obtaining Compounds of Formula Ib

Preferably, the method is conducted by reacting compounds of formula IIb for obtaining compounds of formula Ib with (2S,4R)-configuration Sulfonylation of compound of Formula IIb with a sulfonylhalide (preferably, sulfonylchloride) or sulfonyl anhydride having both a suitable substituent A.

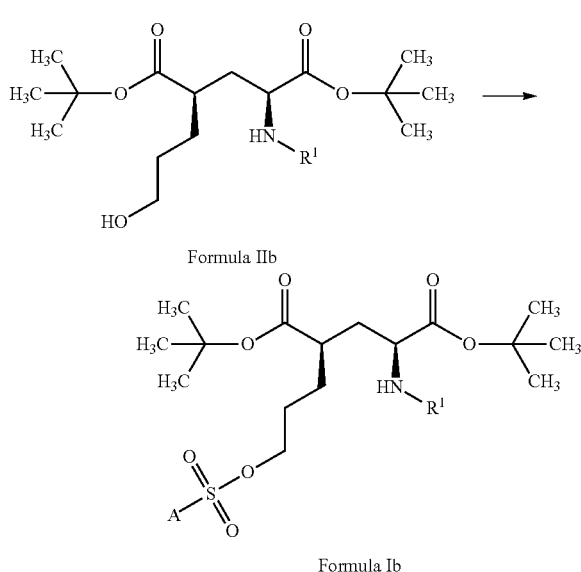

Formula IIb

Formula Ib wherein A and R¹ are defined above.

In another preferred embodiment, the method is conducted by reacting a mixture of compounds of formula IIa and IIb for obtaining a mixture of compounds of formula Ia with (2S,4S)-configuration and compounds of formula Ib with (2S,4R)-configuration that can be separated by methods known to the person skilled in the art (e.g. chromatography, crystallization) to obtain isolated compounds of formula Ia and isolated compounds of formula Ib

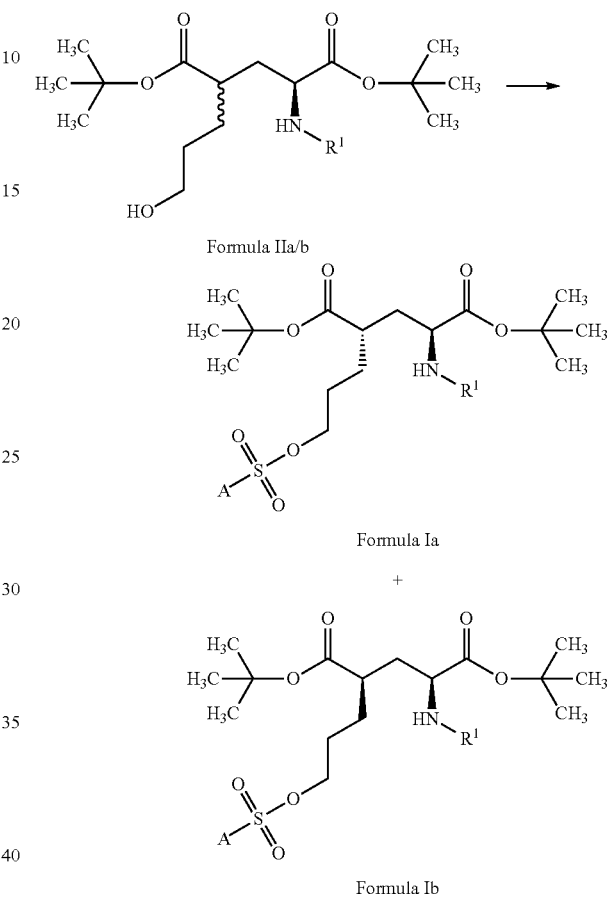

Formula IIa/b

Formula Ia

+

Formula Ib wherein A and R¹ are defined above.

The reagents, solvents and conditions which can be used for this sulfonylation are common and well-known to the skilled person in the field. (J. March, Advanced Organic Chemistry, 4th ed. 1992, John Wiley & Sons, pp 352ff).

The sulfonylation of compounds of formula II to compounds of formula I is performed in a suitable inert solvent, in the presence of a suitable base, optionally in a microwave reactor in case the reaction is performed at an elevated temperature, a temperature between −10° C. and 150° C. and at a pressure up to 5 bar.

Suitable inert solvents are amides such as N,N-dimethylformamide, N,N-dimethylacetamide, or N-methylpyrrolidinone, ethers such as tetrahydrofuran, 1,2-dimethoxyethane, or dioxane, halogenated hydrocarbons such as dichloromethane or chloroform, or others such as or acetonitrile.

Suitable bases are alkali carbonates, such as sodium carbonate or potassium carbonate, alkali bicarbonates such as potassium bicarbonate, or organic bases such as triethylamine, N,N-diisopropylethylamine, pyridine, N-methylmorpholine, N-methylpiperidine, or DBU (1,8-Diazabicyclo (5.4.0)-undec-7-ene).

Preferred inert solvents are dichloromethane or tetrahydrofuran.

Preferred bases are triethylamine, N,N-diisopropylethylamine or pyridine.

The preferred features and embodiments disclosed for compounds of general formula I, Ia, Ib, II, IIa and IIb are herein incorporated.

In a fourth aspect, the invention is directed to methods for obtaining compounds of formula IV-F18.

Method for Obtaining IV-F18: by direct labeling of compounds of formula I

The direct method for obtaining compounds of formula IV-F18 comprises the steps

Reacting compound of Formula I with a $^{18}$F-Fluorination agent to obtain compound of formula III-F18, and Deprotecting the obtained compound of formula III-F18 for obtaining compound of formula IV-F18, wherein compound of formula III-F18 is

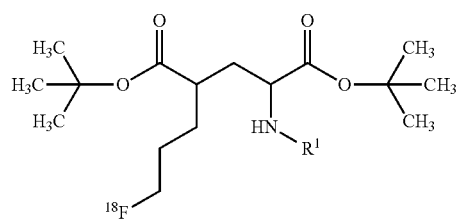

Formula III-F18 wherein $R^1$ is triphenylmethyl (Trityl), and compound of formula IV-F18 is

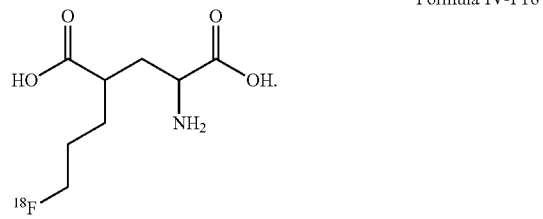

Formula IV-F18

Optionally the method is followed by the purification of compound of Formula IV-F18 by solid-phase-extraction. Preferably solid-phase-extraction cartridges or columns are used.

Preferably, the direct method for obtaining compounds of formula IVa-F18 comprises the steps Reacting compound of Formula Ia with a $^{18}$F-Fluorination agent to obtain compound of formula IIIa-F18, and Deprotecting the obtained compound of formula IIIa-F18 for obtaining compound of formula IVa-F18, wherein compound of formula IIIa-F18 is

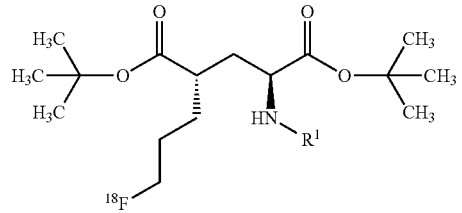

Formula IIIa-F18

$R^1$ is triphenylmethyl (Trityl) and compound of formula IVa-F18 is

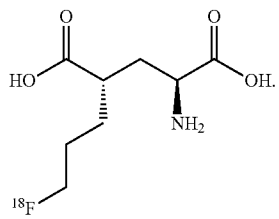

Formula IVa-F18

Optionally the method is followed by the purification of compound of Formula IVa-F18 by solid-phase-extraction. Preferably solid-phase-extraction cartridges or columns are used.

The $^{18}$F-Fluorination agent are exemplified by but not limited to K$^{18}$F, H$^{18}$F, Rb$^{18}$F, Cs$^{18}$F, Na$^{18}$F.

Optionally, the $^{18}$F-Fluorination agent comprises a chelating agent such as a cryptand (e.g.: 4,7,13,16,21,24-Hexaoxa-1,10-diazabicyclo[8.8.8]-hexacosane—Kryptofix®) or a crown ether (e.g.: 18-crown-6).

The $^{18}$F-Fluorination agent can also be a tetraalkylammonium salt of $^{18}$F$^-$ or a tetraalkylphosphonium salt of $^{18}$F$^-$, known to those skilled in the art, e.g.: tetrabutylammonium [$^{18}$F]fluoride, tetrabutylphosphonium [$^{18}$F]fluoride.

Preferably, the $^{18}$F-Fluorination agent is Cs$^{18}$F, K$^{18}$F, tetrabutylammonium [$^{18}$F]fluoride.

The reagents, solvents and conditions which can be used for this fluorination are common and well-known to the skilled person in the field. See, e.g., *J. Fluorine Chem.*, 27 (1985):177-191; Coenen, Fluorine-18 Labeling Methods: Features and Possibilities of Basic Reactions, (2006), in: Schubiger P. A., Friebe M., Lehmann L., (eds), PET-Chemistry—The Driving Force in Molecular Imaging. Springer, Berlin Heidelberg, pp. 15-50). Preferably, the solvents used in the present method are DMF, DMSO, acetonitrile, DMA, THF, or mixtures thereof, preferably the solvent is acetonitrile.

Heating can be done by conventional heating or micro wave heating.

In another preferred embodiment, the direct method for obtaining compounds of formula IVb-F18 comprises the steps Reacting compound of Formula Ib with a $^{18}$F-Fluorination agent to obtain compound of formula IIIb-F18, and Deprotecting the obtained compound of formula IIIb-F18 for obtaining compound of formula IVb-F18, wherein compound of formula IIIb-F18 is

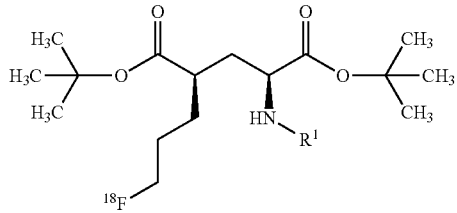

Formula IIIb-F18

R[1] is triphenylmethyl (Trityl) and compound of formula IVb-F18 is

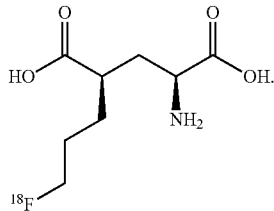

Formula IVb-F18

Optionally the method is followed by the purification of compound of Formula IVb-F18 by solid-phase-extraction. Preferably solid-phase-extraction cartridges or columns are used.

The $^{18}$F-Fluorination agent are exemplified by but not limited to K$^{18}$F, H$^{18}$F, Rb$^{18}$F, Cs$^{18}$F, Na$^{18}$F.

Optionally, the $^{18}$F-Fluorination agent comprises a chelating agent such as a cryptand (e.g.: 4,7,13,16,21,24-Hexaoxa-1,10-diazabicyclo[8.8.8]-hexacosane—Kryptofix®) or a crown ether (e.g.: 18-crown-6).

The $^{18}$F-Fluorination agent can also be a tetraalkylammonium salt of $^{18}$F$^-$ or a tetraalkylphosphonium salt of $^{18}$F$^-$, known to those skilled in the art, e.g.: tetrabutylammonium [$^{18}$F]fluoride, tetrabutylphosphonium [$^{18}$F]fluoride.

Preferably, the $^{18}$F-Fluorination agent is Cs$^{18}$F, K$^{18}$F, tetrabutylammonium [$^{18}$F]fluoride.

The reagents, solvents and conditions which can be used for this fluorination are common and well-known to the skilled person in the field. See, e.g., *J. Fluorine Chem.*, 27 (1985):177-191; Coenen, Fluorine-18 Labeling Methods: Features and Possibilities of Basic Reactions, (2006), in: Schubiger P. A., Friebe M., Lehmann L., (eds), PET-Chemistry—The Driving Force in Molecular Imaging. Springer, Berlin Heidelberg, pp. 15-50). Preferably, the solvents used in the present method are DMF, DMSO, acetonitrile, DMA, THF, or mixtures thereof, preferably the solvent is acetonitrile.

Heating can be done by conventional heating or micro wave heating.

In a preferred embodiment, a compound of formula IV is manufactured by reacting a compound of formula I with a [$^{18}$F]fluoride reagent. Subsequently, protecting groups are cleaved by acidic hydrolysis and compound of formula is purified by solid phase extraction.

More preferably, the [$^{18}$F]fluoride reagent is potassium/[$^{18}$F]fluoride/kryptofix complex.

More preferably, the reaction a compound of formula I with the [$^{18}$F]fluoride reagent is performed in acetonitrile as solvent.

More preferably, 1-25 µmol, even more preferably 1-20 µmol, and even more preferably 5-10 µmol of compound of formula I are used.

More preferably, the compound of formula I is reacted with the [$^{18}$F]fluoride reagent at 60-160° C., more preferably at 80-140° C., even more preferably at 100-140° C.

More preferably, HCl, H$_2$SO$_4$ or H$_3$PO$_4$ is used for acidic hydrolysis. Even more preferably 1M-4M HCl is used for acidic hydrolysis.

More preferably, cation exchange material is used for the purification of compound of formula IV. Even more preferably, MCX cartridge(s) are used for purification of compound of formula IV.

More preferably porous carbon material is used for purification of compound of formula IV.

Even more preferably Hypercarb cartridge(s) are used for purification of compound of formula IV.

In one preferred embodiment the compound of formula I is a compound of formula Ia and the compound of formula IV is a compound of formula IVa In one preferred embodiment the compound of formula I is a compound of formula Ib and the compound of formula IV is a compound of formula IVb In one preferred embodiment, a base is added after acidic hydrolysis. More preferably, NaOH is added after acidic hydrolysis. Even more preferably, 1M-6M NaOH is added and the mixture is heated at 60° C.-100° C.

The preferred features and embodiments disclosed for compounds of general formula I, Ia, Ib, III-F18, IIIa-F18, IIIb-F18, IV-F18, IVa-F18 and IVb-F18 are herein incorporated.

In a fifth aspect, the invention is directed to compounds of formula II

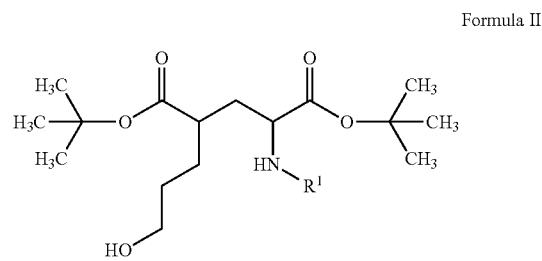

Formula II wherein R[1] is triphenylmethyl (Trityl) and single isomers, tautomers, diastereomers, enantiomers, stereoisomers, stereoisomeric mixtures or mixtures thereof and suitable salts thereof.

Preferably, compounds of formula II relates to compounds with (2S,4S)-configuration (compound of formula IIa)

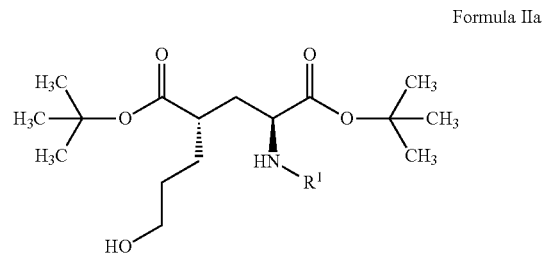

Formula IIa wherein R[1] is triphenylmethyl (Trityl) corresponding to di-tert-butyl (4S)-4-(3-hydroxypropyl)-N-trityl-L-glutamate.

In another preferred embodiment, compounds of formula II relates to compounds with (2S,4R)-configuration (compound of formula IIb)

Formula IIb

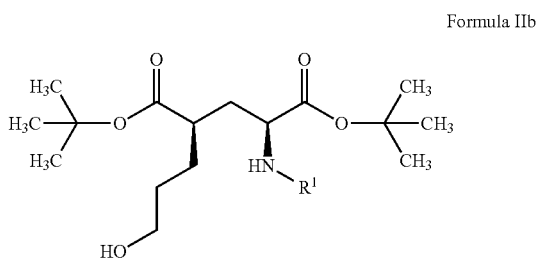

wherein R¹ is triphenylmethyl (Trityl) corresponding to di-tert-butyl (4R)-4-(3-hydroxypropyl)-N-trityl-L-glutamate.

In another preferred embodiment, compounds of formula II relates to compounds with (2S)-configuration (compound of formula IIa/b)

Formula IIa/b

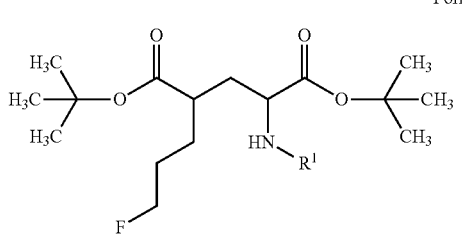

wherein R¹ is triphenylmethyl (Trityl) corresponding to di-tert-butyl 4-(3-hydroxypropyl)-N-trityl-L-glutamate.

In a sixth aspect, the invention is directed to protected compounds of formula III-F Formula III-F

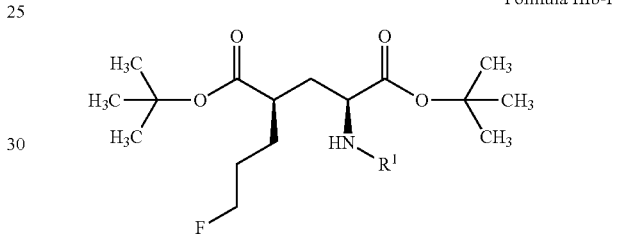

wherein R¹ is triphenylmethyl (Trityl),

F means fluorine atom and single isomers, tautomers, diastereomers, enantiomers, stereoisomers, stereoisomeric mixtures or mixtures thereof and suitable salts thereof.

Preferably, F is $^{18}F$ or $^{19}F$.

More preferably, F is $^{18}F$ (compound of formula III-F18).

Preferably, compounds of formula III relates to compounds with (2S,4S)-configuration (compound of formula IIIa-F)

Formula IIIa-F

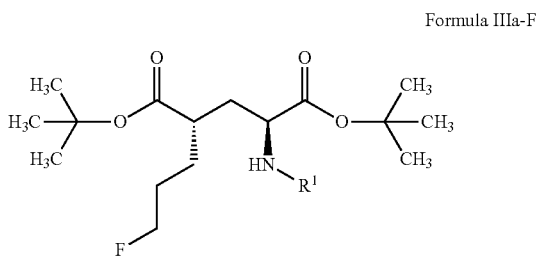

wherein
R¹ is triphenylmethyl (Trityl), and
F means fluorine atom.
Preferably, F is $^{18}F$ in compound of formula IIIa-F.
A preferred compound of Formula IIIa-F18 is di-tert-butyl (4S)-4-(3-[$^{18}F$]Fluoropropyl)-N-trityl-L-glutamate.

In another preferred, compounds of formula III relates to compounds with (2S,4R)-configuration (compound of formula IIIb-F)

Formula IIIb-F wherein
R¹ is triphenylmethyl (Trityl), and
F means fluorine atom.
Preferably, F is $^{18}F$ in compound of formula IIIb-F.
A preferred compound of Formula IIIb-F18 is di-tert-butyl (4R)-4-(3-[$^{18}F$]Fluoropropyl)-N-trityl-L-glutamate.

In a seventh aspect, the invention is directed to a composition comprising compound of formula I, Ia, II, IIa, III-F, IIIa-F, IIIa-F18, IVa-F or IVa-F18 as defined in above aspects and included embodiments. Preferably, the composition comprises compound of formula I, Ia, Ib, II, IIa, IIb, III-F, IIIa-F, IIIb-F, IIIa-F18, IIIb-F18, IVa-F18 or IVb-F18 as defined in above aspects and included embodiments. More preferably, the composition comprises compound of formula I, Ia, Ib, II, IIa, IIb, III-F, IIIa-F, IIIb-F, IIIa-F18, IIIb-F18, as defined in above aspects and included embodiments.

In a first embodiment, the invention is directed to a composition comprising compound of formula I or Ia or IIb and suitable reactants for a fluoro-labeling reaction and/or adjuvants, inter alia, carriers, solvents or stabilizers.

The person skilled in the art is familiar with adjuvants which are suitable for the desired pharmaceutical formulations, preparations or compositions on account of his/her expert knowledge.

Preferably, the composition comprises exemplified compounds, stereoisomers and mixtures thereof, and suitable salts thereof, and acceptable carriers or diluents as described above.

In a second embodiment, the invention is directed to a composition comprising compound of formula II or IIa or IIb as described above and optionally suitable adjuvants. These adjuvants include, inter alia, carriers, solvents, or stabilizers.

The person skilled in the art is familiar with adjuvants which are suitable for the desired pharmaceutical formulations, preparations or compositions on account of his/her expert knowledge.

In a third embodiment, the invention is directed to a composition comprising compound of formula IV-F18 or IVa-F18 or IVb-F18, and pharmaceutically suitable adjuvants. The administration of the compounds, pharmaceutical compositions or combinations according to the invention is performed in any of the generally accepted modes of administration available in the art. Intravenous deliveries are preferred.

In an eighth aspect, the invention is directed to a kit comprising one vial or more than one vial comprising a predetermined quantity of compounds of Formula I, preferably compounds of Formula Ia or Ib. More preferably, the kit comprises compounds of Formula Ia.

Optionally the kit comprises an acceptable carrier, diluent, excipient or adjuvant.

Preferably, the kit comprises predefined quantity of compound of Formula I and one or more solid-phase extraction cartridges/columns for the purification of compound of Formula IV-F18.

Preferably, the Kit comprises physiologically acceptable vehicle or carrier and optional adjuvants and preservatives, reagents suitable to perform the herein disclosed reactions and/or to generate the $^{18}F$ labeling reagents. Furthermore, the kit may contain instructions for its use.

General Synthesis of Compounds of the Invention

Definitions

The terms used in the present invention are defined below but are not limiting the invention scope.

As used herein, the term "precursor" refers to a compound, which can be used as a starting material for a radiolabeling reaction, where an appropriate leaving group of the precursor is replaced by the radioisotope $[^{18}F]$.

As used herein, the term "amine protecting group" refers to a chemical entity (such as, for example triphenylmethyl) chemically bound to an amine group, which inhibits participation of this amine group in chemical reactions (see Greene's Protective Groups in Organic Synthesis, P. Wuts, T. Greene (Wiley)).

As used herein, the term "hydroxyl protecting group" refers to a chemical entity (such as, for example tert-butyl) chemically bound to a hydroxyl group, which inhibits participation of this hydroxyl group in chemical reactions (see Greene's Protective Groups in Organic Synthesis, P. Wuts, T. Greene (Wiley)).

As used herein, the term "alkyl" refers to a $C_1$-$C_6$ straight chain or branched chain alkyl group such as, for example methyl, ethyl, propyl, isopropyl, butyl, isobutyl, tert-butyl, pentyl, isopentyl, neopentyl. Preferably, alkyl is $C_1$-$C_3$ straight chain or branched chain alkyl.

"Aryl" represents a mono- or bicyclic aromatic, carbocyclic bivalent radical having, as a rule, 6 to 10 carbon atoms, optionally substituted by one to four "Substituents"; by way of example and by preference phenyl or naphthyl.

"Biaryl" represents an aromatic radical substituted by an identical aromatic radical. Preferably, Biaryl is biphenyl.

"Heteroaryl" represents an aromatic, mono- or bicyclic bivalent radical having, as a rule, 5 to 10, preferably 5 to 6, ring atoms and up to 3, preferably 1, hetero atoms from the series consisting of S, O and N; by way of example and including but not limited to thienyl, furyl, pyrrolyl, thiazolyl, oxazolyl, imidazolyl, pyridyl, pyrimidyl, pyridazinyl, indolyl, indazolyl, benzofuranyl, benzothiophenyl, quinolinyl, isoquinolinyl, triazolyl, wherein said "Heteroaryl" is optionally substituted by one to four "Substituents". Preferably, "Heteroaryl" is pyridyl or quinolinyl.

As used herein, the term "Arylsulfonyl" refers to aryl groups respectively linked to the respective scaffold by a sulfonyl group, i.e. —S(=O)$_2$—O, with the aryl moiety being as defined above, such as for example p-toluenesulfonyl.

The term "halo" refers to fluoro, chloro, bromo, and iodo.

Whenever the term "substituted" is used, it is meant to indicate that one or more hydrogens at the atom indicated in the expression using "substituted" is/are replaced by one ore multiple moieties from the group comprising halogen, hydroxyl, nitro, $C_1$-$C_6$-alkylcarbonyl, cyano, trifluoromethyl, $C_1$-$C_6$-alkylsulfonyl, $C_1$-$C_6$-alkyl, $C_1$-$C_6$-alkoxy and $C_1$-$C_6$-alkylsulfanyl, provided that the regular valency of the respective atom is not exceeded, and that the substitution results in a chemically stable compound, i.e. a compound that is sufficiently robust to survive isolation to a useful degree of purity from a reaction mixture, and formulation into a pharmaceutical composition.

As used herein, $C_n$-$C_m$ indicates the range of number of carbon atoms the respective moiety may feature, illustrated by but not limited to e.g. $C_1$-$C_6$-alkyl or $C_1$-$C_6$ alkoxy, which may feature 1, 2, 3, 4, 5, or 6 carbon atoms not covering optional additional substitution.

If chiral centres or other forms of isomeric centres are not otherwise defined in a compound according to the present invention, all forms of such stereoisomers, including enantiomers and diastereoisomers, are intended to be covered herein. Compounds containing chiral centres may be used as racemic mixture or as an enantiomerically enriched mixture or as a diastereomeric mixture or as a diastereomerically enriched mixture, or these isomeric mixtures may be separated using well-known techniques, and an individual stereoisomer may be used alone. In cases wherein compounds may exist in tautomeric forms, each tautomeric form is contemplated as being included within this invention whether existing in equilibrium or predominantly in one form.

As used herein, the term "solvents" refers to inorganic such as water, as well as organic compounds such as acetonitrile and their mixtures used for dissolution of other solid, liquid or gaseous compound(s).

Kit

As used herein, the term "kit" refers to a set of the materials (such as filters) and chemicals (such as a precursor or solvents) required for the performing of the single radiolabeling process Radiolabeling As used herein, the term "radiolabeling" refers to a chemical process, where a radioactive isotope (such as $^{18}F$) is attached to a selected molecule (such as a precursor).

Deprotection

As used herein, the term "deprotection" refers to one or more chemical reaction(s), where a protecting chemical group such as trityl is eliminated from the molecule and the functional group of the molecule such as amino-group is re-established Desilylation As used herein, the term "desilylation" refers to one or more chemical reaction(s), where a silyl group $R_3$—Si such as tert-butyldimethylsilyl is eliminated from the molecule and replaced by a proton.

Crystallization

As used herein, the term "crystallization" refers to a physico-chemical process, where a solid crystals are precipitating from a solution, melt or gas.

As used herein, the term "bearing" means or is equivalent to substituted.

EXPERIMENTAL SECTION

| Abbreviations | |
|---|---|
| Boc | tert-Butyloxycarbonyl |
| br | broad signal (in NMR data) |
| d.c. | Corrected for decay |
| Cbz | Carboxybenzoyl |
| CI | chemical ionisation |
| d | Doublet |
| DAD | diode array detector |
| dd | doublet of doublet |
| ddd | doublet of doublet of doublet |
| DIPEA | N,N-Diisopropylethylamine |
| dt | doublet of triplet |
| DMF | N,N-dimethylformamide |
| DMSO | Dimethylsulfoxide |
| EI | electron ionisation |
| ELSD | evaporative light scattering detector |
| ESI | electrospray ionisation |
| EtOAc | ethyl acetate |
| Fmoc | fluorenylmethyloxycarbonyl |
| HPLC | high performance liquid chromatography |
| GBq | Giga Bequerel |
| $K_{2.2.2}$ | 4,7,13,16,21,24-hexaoxa-1,10-diazabicyclo[8.8.8]-hexacosane (Kryptofix 222) |
| $K_{obs}$ | Correspond to the observed reaction rate based on the amount of product measured in the reaction mixture at different time points. |
| $K_{rel}$ | Correspond to the relative reaction rate, precursor used as reference and defined with the value "1". |
| LiHMDS | Lithium bis(trimethylsilyl)amide |
| MBq | Mega Bequerel |
| MS | mass spectrometry |
| MeCN | acetonitrile |
| MTB | methyl tert-butyl ether |
| m | Multiplet |
| mc | centred multiplet |
| m.p. | Melting point |
| n.d.c. | Not decay corrected |
| NMR | nuclear magnetic resonance spectroscopy: chemical shifts (δ) are given in ppm. |
| OPA | Ortho-phthaldialdehyde |
| q | quadruplett (quartet) |
| PMB | para-methoxybenzyl |
| RT | room temperature |
| s | Singlet |
| t | Triplet |
| TBDMS | tert-butyldimethylsilyl |
| trt | Trityl (=triphenylmethyl) |
| tBu, t-Bu, tert-Bu | tert-Butyl |
| THF | Tetrahydrofuran |
| THP | Tetrahydropyran |
| TLC | Thin layer chromatography |

General:

All solvents and chemicals were obtained from commercial sources and used without further purification. Anhydrous solvents and inert atmosphere (nitrogen or argon) were used if not stated otherwise. The preceding table lists the abbreviations used in this paragraph and in the Intermediates and Examples sections as far as they are not explained within the text body. NMR peak forms are stated as they appear in the spectra, possible higher order effects have not been considered.

Reactions were monitored by methods known to the person skilled in the art, such as thin-layer chromatography on suitable stationary phases, such as silica gel coated plates of aluminium or glass, or HPLC/UV analyses.

The compounds and intermediates produced according to the methods of the invention may require purification. Purification of organic compounds is well known to the person skilled in the art and there may be several ways of purifying the same compound. In some cases, no purification may be necessary. In certain cases, the compounds may be purified by crystallization. In some cases, impurities may be removed by trituration using a suitable solvent. In some cases, the compounds may be purified by column chromatography, Column chromatography, as used hereinafter, typically refers to preparative liquid chromatography on a suitable stationary phase, such as commercial silica gel or prepacked silica gel cartridges, e.g. Merck silica gel 60 (230-400 mesh) and eluents such as gradients of ethyl acetate/n-hexane.

Radiolabeling:

All chemicals were purchased from commercial sources, Aldrich and Merck, and used without further purification.

Radiochemical synthesis were performed using a GE MX tracerlab module. Analytical HPLC was performed on an Agilent 1200 system. HPLC solvents were purchased from Aldrich.

General Syntheses

A. Alkylation of Glutamate Backbone

Compounds of the invention can be approached by alkylation of glutamate derivatives A-1 as shown in Scheme 2.

Scheme 2 Alkylation of glutamate backbone ($R^{41}$ is a hydroxyl protecting group, $R^{42}$ is a leaving group, $R^{43}$ is an amine protecting group)

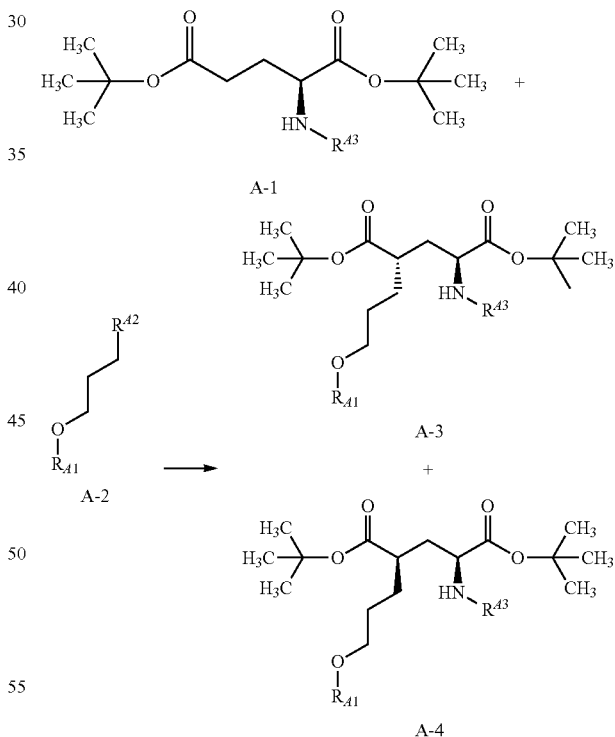

$R^{A2}$ acts as a leaving group (for example Br, I, sulfonate) and $R^{A1}$ is a protecting group. The alkylation of glutamate derivatives is described in the literature, e.g.: M. A. Brimble et al., *Bioorg. Med. Chem.* 2005, 13, 519-523; S. Hanessian et al., *J. Org. Chem.* 2005, 70, 5070-5085; S. Hanessian et al., *Org. Lett.* 2004, 6, 4683-4686; J. Zhang et al., *Tetrahedron Lett.* 2003, 44, 1413-1415. It is well know, that the alkylation affords selectively compounds A-3 if $R^1$ is a carbamate-type protecting group (e.g. Boc, CBz). Mixtures of A-3 and A-4 can be obtained and separated by chromatography methods if other protecting groups are used (e.g. $R^{43}$=Trityl).

Methods are well known to the person skilled in the art to convert compounds of formulae A-3 to compounds of formula IIa, including e.g.:

Cleavage of amine protecting group $R^{43}$ and introduction of amine protecting group $R^1$ (e.g. introduction of Trityl group via triphenylmethyl chloride)

Cleavage of hydroxyl protecting group $R^{41}$ (e.g. desilylation desilylation using TBAF)

Further methods for the synthesis of IIa are well known to the person skilled in the art, e.g. Allylation of A-1 using allyl bromide and subsequent hydroboration.

B. Synthesis of Sulfonates

Precursors for $^{18}$F-alkyl compounds of general Formula I and Ia can be synthesized from the respective hydroxyl compounds of general Formula II and IIa according to methods known in the art (J. March, Advanced Organic Chemistry, 4th ed. 1992, John Wiley & Sons, pp 352ff).

C. $^{18}$F Fluorination

The radiosynthesis of the $^{18}$F labeled compounds of the invention can be accomplished in multiple ways using known methods described in the literature and databases in reach of the person skilled in the art.

More specifically, compounds according to the general Formulae III-F18 and IV-F18 can be synthesized starting from 1 as outlined in Scheme 4. Such nucleophilic fluorinations are known to the person skilled in the art and also described in the literature, for reviews and cited references within see e.g. Cai et al., *Eur. J. Org. Chem.*, 2008, 2853; Ametamey et al., *Chem. Rev.*, 2008, 108, 1501, Miller et al., *Angew. Chem. Int. Ed.* 2008, 47, 8998.

Scheme 4 Synthesis of $^{18}$F-labled compounds of Formula III-F18 and IV-F18

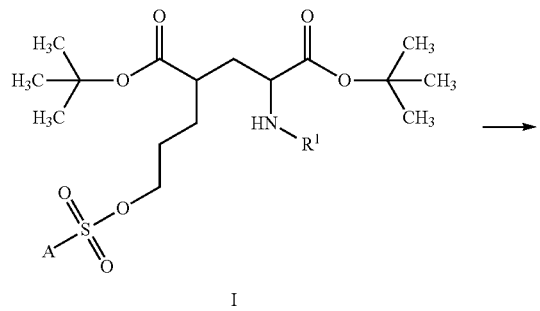

I

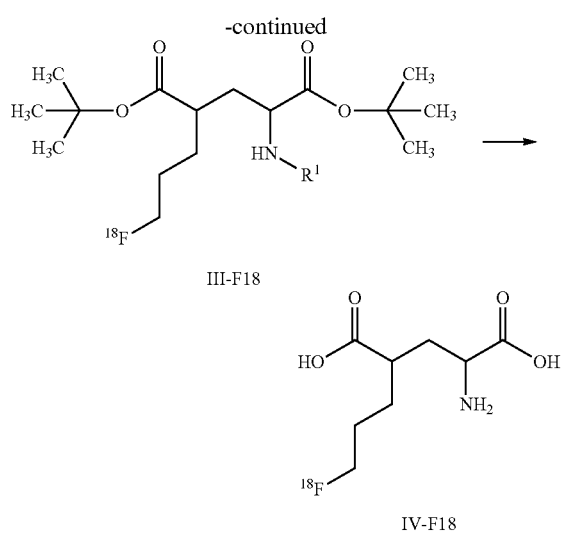

III-F18

IV-F18

HPLC Methods

Method A1 (analytics of di-tert-butyl (4S)-4-(3-hydroxypropyl)-N-trityl-L-glutamate
Column: ChiralPak IA, 4.6×250 mm
Mobile phase: 5% IPA/n-heptane
Flow rate: 1 mL/min
Wavelength: 214/254 nm Method A2 (for Id)
Column: X-Bridge
Mobile phase: Acetonitrile/water 20:80 to 100% water
Flow rate: 1 mL/min
Wavelength: 214 nm Method A3 (for Ia to Ic and Ie to Il)
Column: X-Bridge
Mobile phase: Acetonitrile/water 15:80 to 100% water
Flow rate: 1 mL/min
Wavelength: 214 nm Method A4 ($^{19}$F-fluorination)
Column: Phenomenex Lux 5U Amylose-2
Mobile phase: 10% IPA/Hex
Flow rate: 1 mL/min
Wavelength: 214 nm Method A5 ($^{18}$F-radiolabeling)
Column: Phenomenex Luna 5µ C18(2); 250*4.6 mm
Mobile phase: A: $Na_2HPO_4$ 10 mM pH 7.4, B: acetonitrile
Gradient: 0 min 12% B, 15 min 12% B, 16 min 100% B, 18 min 100% B, 20 min 12% B, 23 min 12% B
Flow rate: 1.2 mL/min
Wavelength: 340 nm
Derivatization: 10 ml of the product solution are mixed with 30 ml OPA reagent (Thermo Scientific, No.:26015). After 1 min reaction at room temperature the solution is applied to the HPLC Preparation of Intermediates I

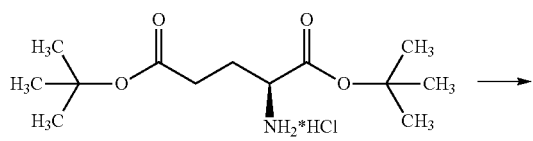

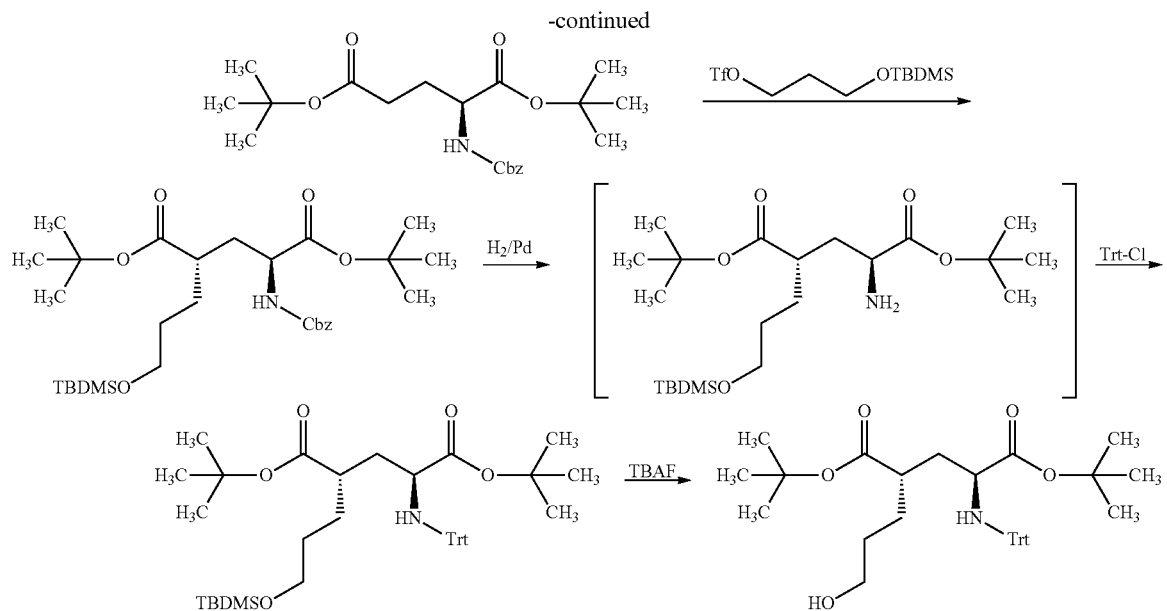

1. Cbz Protection

To a solution of di-tert-butyl L-glutamate hydrochloride (3.0 g, 10.14 mmol) and DIPEA (5.3 mL, 30.4 mmol) in dichloromethane (60 mL) was added a solution of benzyl chloroformate (1.74 mL, 12.2 mmol) in dichloromethane (30 mL). The solution was stirred for 30 min at room temperature. After evaporation of the solvents, the residue was taken up with ethyl acetate and water. The organic phase was separated, washed with water and brine, and was dried over sodium sulfate. After filtration, the solution was evaporated and the crude product was purified by flash chromatography (ethyl acetate/n-hexane: 10/90 to 20/80) to give the desired product (3.65 g, 91%) as a colorless oil.

$^1$H NMR (400 MHz, CDCl$_3$) δ ppm 1.43 (s, 9H), 1.46 (s, 9H), 1.84-1.96 (m, 1H), 2.06-2.18 (m, 1H), 2.20-2.40 (m, 2H), 4.20-4.30 (q, J=8.0 Hz, 1H), 5.10 (s, 2H), 5.34 (d, J=8.0 Hz, 1H), 7.27-7.40 (m, 5H).

2. Alkyation

A solution of di-tert-butyl N-[(benzyloxy)carbonyl]-L-glutamate (4.77 g, 12.12 mmol) in THF (76 mL) was cooled to −78° C. and a 1.0 M solution of lithium bis(trimethylsilyl)amide (25.45 mL, 25.45 mmol) in THF was added slowly. The solution was stirred for 45 min at −78° C., and a solution of 3-(tert-butyldimethylsilyloxy)propyl trifluoromethanesulfonate (5.08 g, 15.76 mmol) in THF (25 mL) was added drop wise at −78° C. After stirring for 2 h, the reaction mixture was quenched with 2.0 N aqueous solution of NH$_4$Cl, and warmed up to room temperature, and concentrated under vacuum. The resulting aqueous solution was extracted with ethyl acetate, the combined organic phase was washed with water and brine, and dried over sodium sulfate. After filtration, the solution was evaporated and the crude product was purified by flash chromatography (ethyl acetate/n-hexane 10/90) to give the desired product (4.62 g, 67%) as a colorless oil.

$^1$H NMR (400 MHz, CDCl$_3$) δ ppm 0.04 (s, 6H), 0.88 (s, 9H), 1.42 (s, 9H), 1.45 (s, 9H), 1.48-1.62 (m, 4H), 1.75-1.86 (m, 1H), 1.90-2.00 (m, 1H), 2.30-2.40 (m, 1H), 3.50-3.62 (m, 2H), 4.16-4.25 (q, J=8.8 Hz, 1H), 5.10 (s, 2H), 5.14 (d, J=8.8 Hz, 1H), 7.28-7.38 (m, 5H); $^{13}$C NMR (100 MHz, CDCl$_3$) δ −5.30, 18.31, 25.93, 27.95, 28.03, 29.12, 30.01, 34.32, 43.14, 53.75, 62.71, 66.89, 80.68, 82.12, 110.00, 128.09, 128.12, 128.46, 136.27, 156.02, 171.53, 174.93; MS (ESI, positive ion mode) C$_{30}$H$_{51}$NO$_7$Si: m/z 588.5 [(M+Na)$^+$].

3. Cbz Deprotection and Trityl Protection

To a solution of di-tert-butyl (4S)-N-[(benzyloxy)carbonyl]-4-(3-{[tert-butyl(dimethyl)silyl]oxy}propyl)-L-glutamate (4.158 g, 7.349 mmol) in MeOH (140 mL) was added 10% Pd/C (2.346 g, 2.2046 mmol) under argon atmosphere. After flushing with hydrogen gas, the solution was suspended for 18 h at room temperature. After filtration with celite, the solution was evaporated. The residue was dissolved in dichloromethane (130 mL). DIPEA (3.5 mL, 20.337 mmol) and triphenylmethyl chloride (2.268 g, 8.135 mmol) were added. The reaction mixture was stirred for 2 h at room temperature, and then water was added. The reaction mixture was extracted with dichloromethane. The combined organic solution was washed with water, and dried over sodium sulfate. After filtration, the solution was evaporated and the crude product was purified by flash chromatography (ethylacetate/n-hexane: 5/95) to give the desired product (3.64 g, 79% overall yield) as a colorless oil.

$^1$H NMR (400 MHz, CDCl$_3$) δ 0.05 (s, 6H), 0.90 (s, 9H), 1.16 (s, 9H), 1.33 (s, 9H), 1.46-1.72 (m, 5H), 2.12-2.22 (m, 1H), 2.28-2.40 (m, 1H), 2.70-2.82 (m, 1H), 3.20-3.30 (m, 1H), 3.59 (t, J=5.6 Hz, 2H), 7.15-7.20 (m, 3H), 7.20-7.28 (m, 6H), 7.42-7.52 (m, 6H); $^{13}$C NMR (100 MHz, CDCl$_3$) δ-5.26, 18.35, 25.98, 27.87, 28.06, 29.93, 30.41, 39.04, 42.67, 55.27, 62.84, 71.14, 80.04, 80.84, 126.31, 127.79, 128.89, 146.35, 174.58, 174.67; MS (ESI) C$_{41}$H$_{59}$NO$_5$Si: m/z 696.9 [(M+Na)$^+$]

4. Desilylation

To a solution of di-tert-butyl (4S)-4-(3-{[tert-butyl(dimethyl)silyl]oxy}propyl)-N-trityl-L-glutamate (3.64 g, 5.40 mmol) in THF (40 mL) was added TBAF (1.0 M in THF, 10.8 mL, 10.8 mmol). The solution was stirred for 1.5 h at room temperature. After evaporation of the solvent, the crude product was purified by flash chromatography (ethyl acetate/n-hexane 40/60) to give the desired product (2.55 g, 84%) as a white solid.

$^1$H NMR (400 MHz, CDCl$_3$) δ ppm 1.15 (s, 9H), 1.32 (s, 9H), 1.50-1.76 (m, 5H), 2.10-220 (m, 1H), 2.30-2.40 (m, 1H), 2.70-2.82 (m, 1H), 3.20-3.30 (m, 1H), 3.61 (t, J=5.6 Hz, 2H), 7.12-7.18 (m, 3H), 7.20-7.28 (m, 6H), 7.42-7.50 (m, 6H); $^{13}$C NMR (100 MHz, CDCl$_3$) δ 27.86, 28.04, 29.59, 30.26, 39.10, 42.63, 55.27, 62.49, 71.16, 80.33, 80.96, 126.34, 127.80, 128.87, 146.29, 174.63, 174.68; MS (ESI) C$_{35}$H$_{45}$NO$_5$: m/z 582.6 [(M+Na)$^+$]

Chiral HPLC analysis of di-tert-butyl (4S)-4-(3-hydroxypropyl)-N-trityl-L-glutamate was done according the method A1 (retention time: 7-8 min).

General Procedures $^{19}$F-Fluorination:

Precursor (0.01 mmol) was dissolved in acetonitrile (0.5 mL), and 1.0 M TBAF/acetonitrile solution (20 μL, 0.02 mmol) was added. The reaction mixture was stirred at 80° C. for 2 h. 40 μL of solution was taken at 5, 10, 20, 40, 60, 90, and 120 min for HPLC analysis (method A4).

$^{18}$F-Fluorination:

[$^{18}$F]Fluoride (380-1400 MBq) was trapped on a QMA cartridge (Waters, SepPak light). The activity was eluted with 0.6 mL kryptofix2.2.2/potassium carbonate solution (3 mg/0.6 mg) in acetonitrile/water into the reaction vessel. The mixture was dried (95° C., nitrogen stream, vacuum). 6 mg of precursor in 1.5 mL acetonitrile were added to the dried residue and the resulting solution was stirred at 120° C. (displayed reactor temperature) for 5 min. Subsequently, approx. 1.5 mL 2 M HCl was added. The mixture was heated at 120° C. for 4.2 min.

The reaction mixture was diluted with 10 ml water and was transferred to 2 MCX cartridges (Waters, Oasis MCX plus extraction cartridge). The cartridges were washed with 10 ml of water and subsequently eluted with 15 ml phosphate buffer (containing 10.5 mg Na$_2$HPO$_4$×2H$_2$O, 9 mg NaCl). The product solution is transferred via a Hypercarb cartridge (Thermo Scientific, Hypersep Hypercarb 500 mg/6 ml) to the final product vial.

HPLC analytics of the resulting product is performed using method A5.

Identity of IV-F18 was confirmed by co-elution with reference compound IV-F19 and UV detection at 340 nm (retention time: 12-13 min).

Example Compounds of the Invention (Precursor Compounds) I

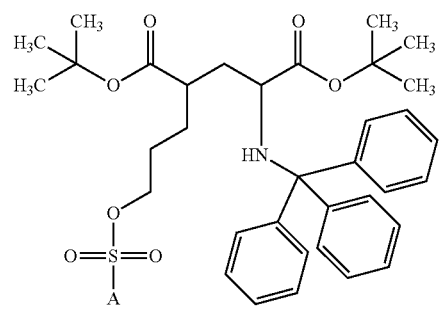

Formula I

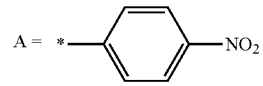

Ia

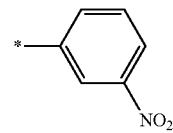

Ib

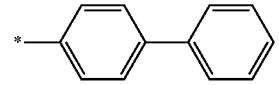

Ic

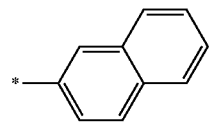

Id

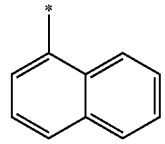

Ie

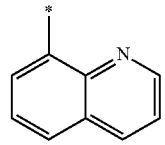

If

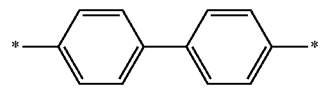

Ig

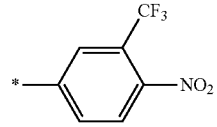

Ih

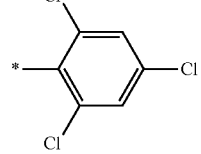

Ii

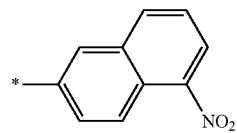

Ij

Ia Di-tert-butyl (4S)-4-(3-{[(4-nitrophenyl)sulfonyl]oxy}propyl)-N-trityl-L-glutamate

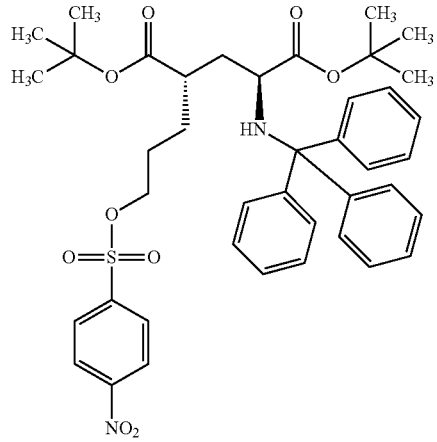 [SMILES: CC(C)(C)OC(=O)[C@@H](CCCOS(=O)(=O)c1ccc([N+](=O)[O-])cc1)C[C@H](NC(c1ccccc1)(c1ccccc1)c1ccccc1)C(=O)OC(C)(C)C]

To a solution of di-tert-butyl (4S)-4-(3-hydroxypropyl)-N-trityl-L-glutamate (212.6 mg, 0.38 mmol) and triethylamine (159 μL, 1.14 mmol) in dichloromethane (5 mL) was added 4-nitrobenzenesulfonyl chloride (126 mg, 0.57 mmol) at 0° C. The reaction mixture was stirred at 0° C. for 2 h and then water was added. The organic layer was separated, and aqueous layer was extracted with dichloromethane. The combined organic solution was dried over sodium sulfate, and concentrated in vacuo. The residue was purified by flash column chromatography (ethyl acetate/n-hexane=15/85) to give the desired product (231 mg, 82%) as a white solid.

$^1$H NMR (400 MHz, CDCl$_3$) δ ppm 1.14 (s, 9H), 1.30 (s, 9H), 1.50-1.73 (m, 5H), 2.00-2.12 (m, 1H), 2.22-2.32 (m, 1H), 2.75 (d, J=9.2 Hz, 1H), 3.20-3.27 (m, 1H), 4.12 (t, J=6.4 Hz, 2H), 7.14-7.19 (m, 3H), 7.20-7.27 (m, 6H), 7.42-7.47 (m, 6H), 8.09 (d, J=8.8 Hz, 2H), 8.38 (d, J=8.8 Hz, 2H); $^{13}$C NMR (100 MHz, CDCl$_3$) δ 26.63, 27.83, 28.00, 29.03, 38.57, 42.20, 55.16, 71.18, 71.34, 80.64, 81.05, 124.48, 126.41, 127.83, 128.81, 129.20, 141.86, 146.17, 173.87, 174.33; MS (ESI, positive ion mode) C$_{41}$H$_{48}$N$_2$O$_9$S: m/z 767.6 [M+Na]+.

Ib Di-tert-butyl (4S)-4-(3-{[(3-nitrophenyl)sulfonyl]oxy}propyl)-N-trityl-L-glutamate

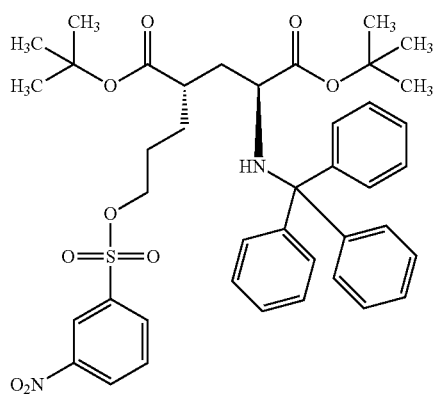 [SMILES: CC(C)(C)OC(=O)[C@@H](CCCOS(=O)(=O)c1cccc([N+](=O)[O-])c1)C[C@H](NC(c1ccccc1)(c1ccccc1)c1ccccc1)C(=O)OC(C)(C)C]

To a solution of di-tert-butyl (4S)-4-(3-hydroxypropyl)-N-trityl-L-glutamate (206.2 mg, 0.37 mmol) and triethylamine (154 μL, 1.10 mmol) in dichloromethane (5 mL) was added 3-nitrobenzenesulfonyl chloride (122 mg, 0.55 mmol) at 0° C. The reaction mixture was stirred at 0° C. for 2 h and then water was added. The organic layer was separated, and aqueous layer was extracted with dichloromethane. Combined organic solution was dried over sodium sulfate, and concentrated in vacuo. The residue was purified by flash column chromatography (ethyl acetate/n-hexane=20/80) to give the desired product (215 mg, 78%) as a white solid.

$^1$H NMR (400 MHz, CDCl$_3$) δ ppm 1.14 (s, 9H), 1.30 (s, 9H), 1.50-1.73 (m, 5H), 2.03-2.12 (m, 1H), 2.23-2.32 (m, 1H), 2.75 (d, J=8.4 Hz, 1H), 3.20-3.27 (m, 1H), 4.13 (t, J=6.4 Hz, 2H), 7.14-7.19 (m, 3H), 7.20-7.27 (m, 6H), 7.42-7.47 (m, 6H), 7.77 (t, J=8.2 Hz, 1H), 8.22 (dq, J=0.8, 8.0 Hz, 1H), 8.50 (dq, J=0.8, 8.0 Hz, 1H), 8.75 (t, J=1.8 Hz, 1H); $^{13}$C NMR (100 MHz, CDCl$_3$) δ 26.63, 27.82, 27.97, 29.03, 38.65, 42.24, 55.12, 71.14, 71.32, 80.62, 81.03, 123.13, 126.38, 127.80, 128.18, 128.81, 130.74, 133.24, 138.31, 146.17, 173.84, 174.34; MS (ESI, positive ion mode) C$_{41}$H$_{48}$N$_2$O$_9$S: m/z 767.8 [M+Na]+.

Ic Di-tert-butyl (4S)-4-{3-[(biphenyl-4-ylsulfonyl)oxy]propyl}-N-trityl-L-glutamate

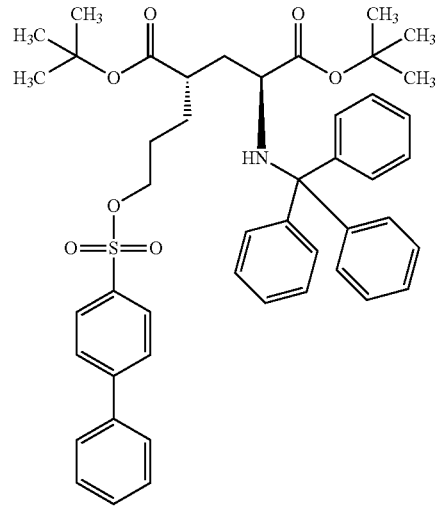 [SMILES: CC(C)(C)OC(=O)[C@@H](CCCOS(=O)(=O)c1ccc(-c2ccccc2)cc1)C[C@H](NC(c1ccccc1)(c1ccccc1)c1ccccc1)C(=O)OC(C)(C)C]

To a solution of di-tert-butyl (4S)-4-(3-hydroxypropyl)-N-trityl-L-glutamate (202.8 mg, 0.36 mmol) and triethylamine (151 μL, 1.09 mmol) in dichloromethane (5 mL) was added biphenyl-4-sulfonyl chloride (137 mg, 0.54 mmol) at 0° C. The reaction mixture was stirred at 0° C. for 5 h and then water was added. The organic layer was separated, and aqueous layer was extracted with dichloromethane. Combined organic solution was dried over sodium sulfate, and concentrated in vacuo. The residue was purified by flash column chromatography (ethyl acetate/n-hexane=10/90) to give the desired product (236 mg, 84%) as a white solid.

$^1$H NMR (400 MHz, CDCl$_3$) δ ppm 1.14 (s, 9H), 1.30 (s, 9H), 1.50-1.73 (m, 5H), 2.03-2.12 (m, 1H), 2.23-2.32 (m, 1H), 2.70-2.80 (m, 1H), 3.18-3.27 (m, 1H), 4.06 (t, J=6.4 Hz, 2H), 7.12-7.17 (m, 3H), 7.20-7.27 (m, 6H), 7.40-7.52 (m, 9H), 7.58-7.62 (m, 2H), 7.72-7.76 (m, 2H), 7.94-7.98 (m, 2H); $^{13}$C NMR (100 MHz, CDCl$_3$) δ 26.66, 27.85, 28.00, 29.26, 38.74, 42.35, 55.14, 70.38, 71.16, 80.51, 80.99, 126.37, 127.38, 127.81, 127.86, 128.39, 128.70, 128.84, 129.10, 134.50, 139.04, 146.21, 146.72, 173.98, 174.41; MS (ESI, positive ion mode) C$_{47}$H$_{53}$NO$_7$S: m/z 798.5 [M+Na]$^+$.

Id Di-tert-butyl (4S)-4-{3-[(2-naphthylsulfonyl)oxy]propyl}-N-trityl-L-glutamate

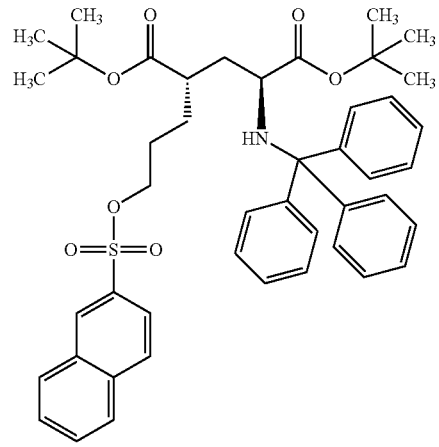 [SMILES: CC(C)(C)OC(=O)[C@@H](CCCOS(=O)(=O)c1ccc2ccccc2c1)C[C@H](NC(c1ccccc1)(c1ccccc1)c1ccccc1)C(=O)OC(C)(C)C]

To a solution of di-tert-butyl (4S)-4-(3-hydroxypropyl)-N-trityl-L-glutamate (217.5 mg, 0.39 mmol) and triethylamine (160 μL, 1.17 mmol) in dichloromethane (5.0 mL) was added naphthalene-2-sulfonyl chloride (155.4 mg, 0.58 mmol) at 0° C. The reaction mixture was stirred at 0° C. for 3 h and then water was added. The organic layer was separated, and aqueous layer was extracted with dichloromethane. Combined organic solution was dried over sodium sulfate, and concentrated in vacuo. The residue was purified by flash column chromatography (ethyl acetate/n-hexane=12/88) to give the desired product (289 mg, 82%) as a white solid (m.p.=119.3° C.).

$^1$H NMR (400 MHz, CDCl$_3$) δ 1.12 (s, 9H), 1.27 (s, 9H), 1.50-1.70 (m, 5H), 2.00-2.10 (m, 1H), 2.22-2.32 (m, 1H), 2.74 (d, J=8.8 Hz, 1H), 3.14-3.24 (m, 1H), 4.04 (t, J=6.4 Hz, 2H), 7.10-7.16 (m, 3H), 7.18-7.24 (m, 6H), 7.40-7.46 (m, 6H), 7.60-7.72 (m, 2H), 7.85 (dd, J=1.6, 8.0 Hz, 1H), 7.93 (d, J=8.0 Hz, 1H), 7.96-8.02 (m, 2H), 8.48 (d, J=1.2 Hz, 1H); $^{13}$C NMR (100 MHz, CDCl$_3$) δ 26.6, 27.8, 27.9, 29.2, 38.7, 42.3, 55.1, 70.4, 71.1, 80.5, 80.9, 122.5, 126.3, 127.8, 128.0, 128.8, 129.3, 129.7, 131.9, 132.8, 135.2, 146.2, 173.9, 174.4; MS (ESI, positive ion mode) C$_{45}$H$_{51}$NO$_7$S: m/z 772.9 [M+Na]$^+$.

Ie Di-tert-butyl (4S)-4-{3-[(1-naphthylsulfonyl)oxy]propyl}-N-trityl-L-glutamate

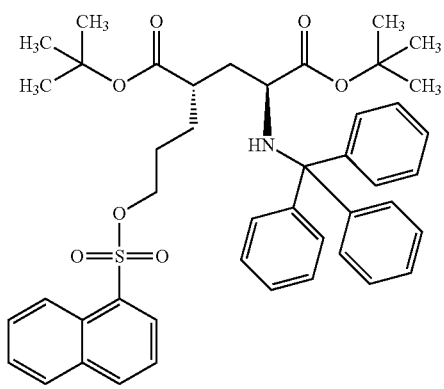 [SMILES: CC(C)(C)OC(=O)[C@@H](CCCOS(=O)(=O)c1cccc2ccccc12)C[C@H](NC(c1ccccc1)(c1ccccc1)c1ccccc1)C(=O)OC(C)(C)C]

To a solution of di-tert-butyl (4S)-4-(3-hydroxypropyl)-N-trityl-L-glutamate (216.8 mg, 0.39 mmol) and triethylamine (160 μL, 1.16 mmol) in dichloromethane (5.0 mL) was added naphthalene-1-sulfonyl chloride (131.7 mg, 0.58 mmol) at 0° C. The reaction mixture was stirred at 0° C. for 3 h and then water was added. The organic layer was separated, and aqueous layer was extracted with dichloromethane. Combined organic solution was dried over sodium sulfate, and concentrated in vacuo. The residue was purified by flash column chromatography (ethyl acetate/n-hexane=12/88) to give the desired product (248 mg, 85%) as a white solid.

$^1$H NMR (400 MHz, CDCl$_3$) δ 1.12 (s, 9H), 1.25 (s, 9H), 1.48-1.64 (m, 5H), 1.96-2.18 (m, 1H), 2.16-2.26 (m, 1H), 2.73 (d, J=9.2 Hz, 1H), 3.10-3.20 (m, 1H), 3.90-4.00 (m, 2H), 7.10-7.16 (m, 3H), 7.18-7.24 (m, 6H), 7.40-7.46 (m, 6H), 7.56 (t, J=7.6 Hz, 1H), 7.62 (t, J=8.0 Hz, 1H), 7.69 (t, J=7.6 Hz, 1H), 7.96 (d, J=8.0 Hz, 1H), 8.13 (d, J=8.4 Hz, 1H), 8.28 (d, J=7.2 Hz, 1H), 8.60 (d, J=8.4 Hz, 1H); $^{13}$C NMR (100 MHz, CDCl$_3$) δ 26.5, 27.8, 27.9, 29.2, 38.7, 42.3, 55.0, 70.5, 71.1, 80.4, 80.9, 124.0, 124.9, 126.3, 127.2, 127.8, 128.4, 128.7, 128.80, 128.83, 130.4, 131.2, 134.1, 135.2, 146.2, 173.9, 174.4; MS (ESI, positive ion mode) C$_{45}$H$_{51}$NO$_7$S: m/z 772.8 [M+Na]$^+$.

If Di-tert-butyl (4S)-4-{3-[(quinolin-8-ylsulfonyl)oxy]propyl}-N-trityl-L-glutamate

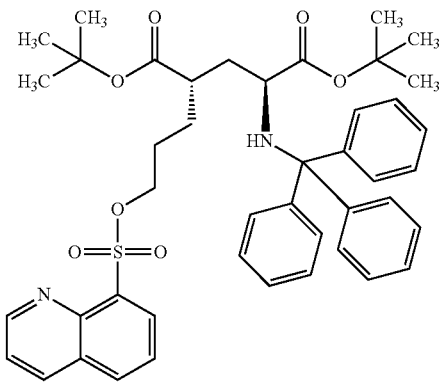 [SMILES: CC(C)(C)OC(=O)[C@@H](CCCOS(=O)(=O)c1cccc2cccnc12)C[C@H](NC(c1ccccc1)(c1ccccc1)c1ccccc1)C(=O)OC(C)(C)C]

To a solution of di-tert-butyl (4S)-4-(3-hydroxypropyl)-N-trityl-L-glutamate (203.4 mg, 0.36 mmol) and triethylamine (150 μL, 1.09 mmol) in dichloromethane (5.0 mL) was added quinoline-8-sulfonyl chloride (124.1 mg, 0.55 mmol) at 0° C. The reaction mixture was stirred at 0° C. for 3 h and at room temperature for overnight and then water was added. The organic layer was separated, and aqueous layer was extracted with dichloromethane. Combined organic solution was dried over sodium sulfate, and concentrated in vacuo. The residue was purified by flash column chromatography (MeOH/CH$_2$Cl$_2$=1/99) to give the desired product (140 mg, 51%) as a white solid.

$^1$H NMR (400 MHz, CDCl$_3$) δ 1.11 (s, 9H), 1.26 (s, 9H), 1.46-1.74 (m, 5H), 2.00-2.30 (m, 1H), 2.20-2.28 (m, 1H), 2.72 (d, J=9.2 Hz, 1H), 3.12-3.22 (m, 1H), 4.31 (t, J=6.4 Hz, 2H), 7.12-7.16 (m, 3H), 7.20-7.26 (m, 6H), 7.40-7.46 (m, 6H), 7.56 (dd, J=8.4, 4.2 Hz, 1H), 7.53-7.68 (m, 1H), 8.12 (dd, J=8.2, 1.6 Hz, 1H), 8.26 (dd, J=2.0, 8.2 Hz, 1H), 8.50 (dd, J=7.2, 1.6 Hz, 1H), 9.16 (dd, J=1.6, 4.2 Hz, 1H); $^{13}$C NMR (100 MHz, CDCl$_3$) δ 26.9, 27.8, 27.9, 29.4, 38.8, 42.4, 55.1, 71.1, 71.5, 80.4, 80.9, 122.4, 125.2, 126.3, 127.8, 128.8, 129.0, 133.1, 134.6, 136.4, 146.2, 151.9, 173.9, 174.4; MS (ESI, positive ion mode) C$_{44}$H$_{50}$N$_2$O$_7$S: m/z 773.9 [M+Na]$^+$.

Ig Tetra-tert-butyl (2S,4S,2'S,4'S)-2,2'-[biphenyl-4,4'-diylbis(sulfonyloxypropane-3,1-diyl)]bis[4-(tritylamino)pentanedioate]

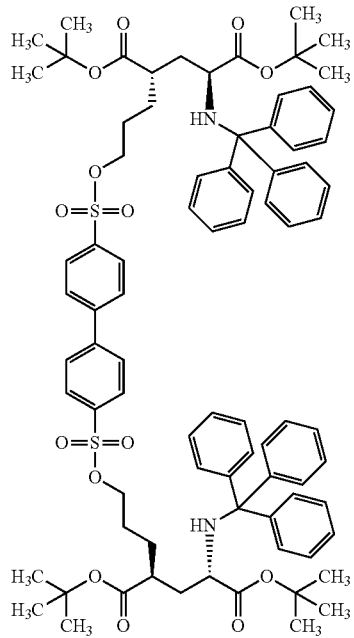 [SMILES: CC(C)(C)OC(=O)[C@@H](CCCOS(=O)(=O)c1ccc(-c2ccc(S(=O)(=O)OCCC[C@@H](C[C@H](NC(c3ccccc3)(c3ccccc3)c3ccccc3)C(=O)OC(C)(C)C)C(=O)OC(C)(C)C)cc2)cc1)C[C@H](NC(c1ccccc1)(c1ccccc1)c1ccccc1)C(=O)OC(C)(C)C]

To a solution of di-tert-butyl (4S)-4-(3-hydroxypropyl)-N-trityl-L-glutamate (209.6 mg, 0.37 mmol, 2.2 eq) and triethylamine (140 µL, 1.02 mmol) in dichloromethane (5.0 mL) was added biphenyl-4-4'-disulfonyl chloride (60 mg, 0.17 mmol) at 0° C. The reaction mixture was stirred at 0° C. for 3 h and at room temperature for overnight and then water was added. The organic layer was separated, and aqueous layer was extracted with dichloromethane. Combined organic solution was dried over sodium sulfate, and concentrated in vacuo. The residue was purified by flash column chromatography (ethyl acetate/n-hexane=25/75) to give the desired product (98.7 mg, 41%) as a white solid.

$^1$H NMR (400 MHz, CDCl$_3$) δ 1.16 (s, 9H), 1.30 (s, 9H), 1.50-1.76 (m, 5H), 2.04-2.14 (m, 1H), 2.24-2.34 (m, 1H), 2.75 (d, J=9.2 Hz, 1H), 3.18-3.28 (m, 1H), 4.08 (t, J=6.4 Hz, 2H), 7.12-7.18 (m, 3H), 7.20-7.26 (m, 6H), 7.40-7.46 (m, 6H), 7.72 (d, J=8.4 Hz, 2H), 8.00 (d, J=8.4 Hz, 1H); $^{13}$C NMR (100 MHz, CDCl$_3$) δ 26.6, 27.8, 28.0, 29.2, 38.6, 42.3, 55.1, 70.6, 71.2, 80.5, 81.0, 126.4, 127.8, 128.2, 128.6, 128.8, 136.1, 144.4, 146.2, 174.0, 174.4; MS (ESI, positive ion mode) C$_{82}$H$_{96}$N$_2$O$_{14}$S$_2$: m/z 1420.6 [M+Na]$^+$.

Ih Di-tert-butyl (4S)-4-[3-({[4-nitro-3-(trifluoromethyl)phenyl]sulfonyl}oxy)propyl]-N-trityl-L-glutamate

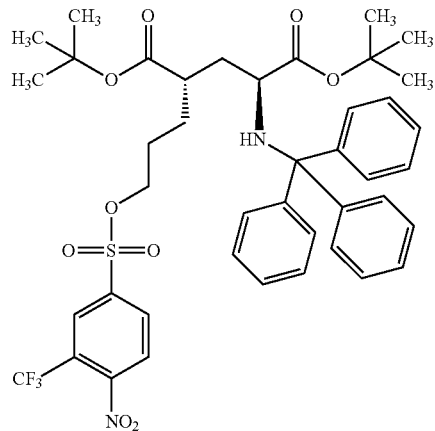 [SMILES: CC(C)(C)OC(=O)[C@@H](CCCOS(=O)(=O)c1ccc([N+](=O)[O-])c(C(F)(F)F)c1)C[C@H](NC(c1ccccc1)(c1ccccc1)c1ccccc1)C(=O)OC(C)(C)C]

To a solution of di-tert-butyl (4S)-4-(3-hydroxypropyl)-N-trityl-L-glutamate (439 mg, 0.78 mmol) and triethylamine (330 µL, 2.35 mmol) in dichloromethane (7.0 mL) was added 4-nitro-3-(trifluoromethyl)benzenesulfonyl chloride (340.7 mg, 1.18 mmol) at 0° C. The reaction mixture was stirred at 0° C. for 45 min and then water was added. Organic layer was separated, and aqueous layer was extracted with dichloromethane. Combined organic solution was dried over sodium sulfate, and concentrated in vacuo. The residue was purified by flash column chromatography (ethyl acetate/n-hexane=15/85) to give the desired product (4 h, 470 mg, 74%) as a light yellow solid.

$^1$H NMR (400 MHz, CDCl$_3$) δ 1.14 (s, 9H), 1.30 (s, 9H), 1.52-1.80 (m, 5H), 2.04-2.14 (m, 1H), 2.24-2.34 (m, 1H), 2.76 (d, J=8.8 Hz, 1H), 3.20-3.28 (m, 1H), 4.17 (t, J=6.0 Hz, 2H), 7.16-7.20 (m, 3H), 7.20-7.28 (m, 6H), 7.42-7.48 (m, 6H), 7.97 (d, J=8.4 Hz, 1H), 8.23 (dd, J=2.0, 8.4 Hz, 1H), 8.34 (d, J=1.6 Hz, 1H); MS (ESI, positive ion mode) C$_{42}$H$_{47}$F$_3$N$_2$O$_9$S: m/z 835.4 [M+Na]$^+$.

Ii Di-tert-butyl (4S)-4-(3-{[(2,4,6-trichlorophenyl)sulfonyl]oxy}propyl)-N-trityl-L-glutamate

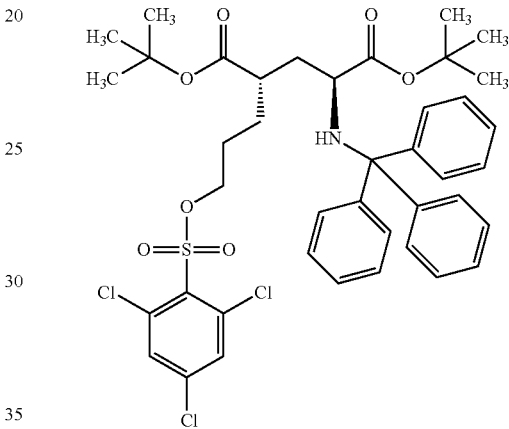

To a solution of di-tert-butyl (4S)-4-(3-hydroxypropyl)-N-trityl-L-glutamate (438 mg, 0.78 mmol) and triethylamine (327 µL, 2.35 mmol) in dichloromethane (7.0 mL) was added 2,4,6-trichlorobenzenesulfonyl chloride (328.6 mg, 1.17 mmol) at 0° C. The reaction mixture was stirred at 0° C. for 1 h and then water was added. The organic layer was separated, and aqueous layer was extracted with dichloromethane. Combined organic solution was dried over sodium sulfate, and concentrated in vacuo. The residue was purified by flash column chromatography (ethyl acetate/n-hexane=10/90) to give the desired product (415 mg, 66%) as a white solid.

$^1$H NMR (400 MHz, CDCl$_3$) δ 1.15 (s, 9H), 1.31 (s, 9H), 1.52-1.80 (m, 5H), 2.04-2.16 (m, 1H), 2.26-2.36 (m, 1H), 2.77 (d, J=9.6 Hz, 1H), 3.18-3.24 (m, 1H), 4.15 (t, J=6.4 Hz, 2H), 7.12-7.18 (m, 3H), 7.20-7.28 (m, 6H), 7.42-7.48 (m, 6H), 7.50 (s, 2H); $^{13}$C NMR (100 MHz, CDCl$_3$) δ 26.5, 27.8, 28.0, 29.2, 38.7, 42.2, 55.1, 71.1, 71.4, 80.5, 81.0, 126.3, 127.8, 128.8, 130.9, 131.2, 136.7, 139.3, 146.1, 173.8, 174.3; MS (ESI, positive ion mode) C$_{41}$H$_{46}$Cl$_3$NO$_7$S: m/z 826.3 [M+Na]$^+$.

Ij Di-tert-butyl (4S)-4-(3-{[(7-nitro-2-naphthyl)sulfonyl]oxy}propyl)-N-trityl-L-glutamate

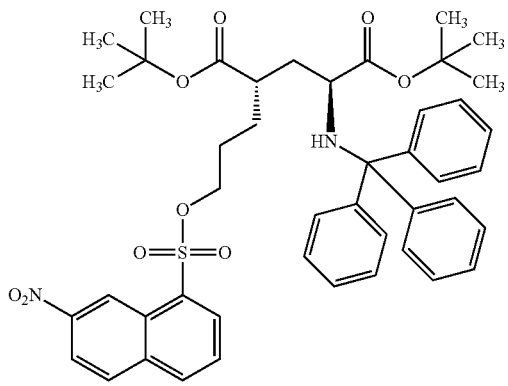 [SMILES: CC(C)(C)OC(=O)[C@@H](CCCOS(=O)(=O)c1cccc2ccc([N+](=O)[O-])cc12)C[C@H](NC(c1ccccc1)(c1ccccc1)c1ccccc1)C(=O)OC(C)(C)C]

To a solution of di-tert-butyl (4S)-4-(3-hydroxypropyl)-N-trityl-L-glutamate (486 mg, 0.84 mmol) and triethylamine (350 µL, 2.58 mmol) in dichloromethane (7.0 mL) was added 5-nitro-naphthalene-2-sulfonyl chloride (340.8 mg, 1.25 mmol) at 0° C. The reaction mixture was stirred at 0° C. for 2 h and water was added. The organic layer was separated, and aqueous layer was extracted with dichloromethane. Combined organic solution was dried over sodium sulfate, and concentrated in vacuo. The residue was purified by flash column chromatography (ethyl acetate/n-hexane=20/80) to give the desired product (616 mg, 93%) as a white solid.

$^1$H NMR (400 MHz, CDCl$_3$) δ 1.12 (s, 9H), 1.28 (s, 9H), 1.48-1.74 (m, 5H), 2.00-2.12 (m, 1H), 2.20-2.30 (m, 1H), 2.74 (d, J=8.0 Hz, 1H), 3.12-3.24 (m, 1H), 4.11 (t, J=6.4 Hz, 2H), 7.10-7.18 (m, 3H), 7.18-7.26 (m, 6H), 7.38-7.46 (m, 6H), 7.73 (t, J=7.6 Hz, 1H), 8.04-8.10 (m, 1H), 8.25 (d, J=8.4 Hz, 1H), 8.43 (d, J=7.6 Hz, 1H), 8.58 (s, 1H), 8.77 (d, J=9.2 Hz, 1H); $^{13}$C NMR (100 MHz, CDCl$_3$) δ 26.6, 27.8, 28.0, 29.1, 38.6, 42.2, 55.1, 70.9, 71.1, 80.5, 81.0, 125.4, 125.9, 126.3, 127.01, 127.04, 127.8, 128.8, 129.8, 133.0, 134.8, 135.8, 146.2, 146.4, 173.9, 174.3; MS (ESI, positive ion mode) C$_{45}$H$_{50}$N$_2$O$_9$S: m/z 817.5 [M+Na]$^+$.

Crystallization

Crystallization was done for compound Id. 2% ether/hexane was used for this crystallization. Crystallization was obtained for compound Id.

$^{19}$F-Fluorination of Example Compounds $^{19}$F-Fluorination was performed as described in "General procedures". The progress of the reaction was examined after 5, 10, 20, 40, 60, 90, and 120 min. Plotting the percentage of the conversation versus the time, the reaction rates were calculated. For calculation of the relative reaction rates, the slowest reaction ($^{19}$F-fluorination of If) was defined as 1. Fastest conversion was found for the compounds Ia, Ib and especially for Ig. The compounds Ic, Id, Ie; Ii and Ij exhibited similar reaction rates compared to If.

$^{18}$F-Fluorination of Example Compounds I $^{18}$F-Fluorination was performed as described in "General procedures". Radiochemical yields and purities as shown in table 2 were determined.

The radiochemical yield was calculated by the ratio of product radioactivity and starting radioactivity. Both are measured using a dose calibrator (MED Nuklearmedizin Technik Dresden). The radiochemical purity is determined by analytical HPLC (method A5).

TABLE 2

| | Radiolabeling of precursors | |
|---|---|---|
| Precursor | Epimeric Ratio (4S:4R) | Radiochemical yield % (d.c) |
| Ia | 97/3 | 40 |
| Ib | 95/5 | 50 |
| Ic | 94/6 | 52 |
| Id | 99/1 | 46 |
| Ie | 95/5 | 56 |
| If | 97/3 | 38 |
| Ig | 94/6 | 45 |
| Ii | 93/7 | 51 |
| Ij | 99/1 | 39 |

Table 2 indicates that for all compounds high radiochemical yields (38-56% n.d.c.) have been obtained.

Furthermore, table 2 shows that the radiolabeling resulted in high stereochemical purities for the compounds Ia-Ij (93/7-99/1).

Stability of Example Compounds

The stability of the compounds of formula I were examined in solid form at two different temperatures: 0° C., and −20° C. The precursors were tested weekly for 4 weeks. Before the study, purities of the precursors were determined individually by HPLC analysis.

Compound Sampling

1. Solid state: 3-5 mg of the respective precursor Ia to Ij were put into 8 amber vials, which were flushed with Ar gas and capped. Each four vials containing precursor were stored at 0° C., and −20° C. Every week for 4 weeks, 1 mg of precursor was dissolved in acetonitrile (1.0 mL). 10 µL of solution was injected into HPLC (method A2 or A3, respectively).

TABLE 1

| Reaction rates of precursors | | | | | | | | | |
|---|---|---|---|---|---|---|---|---|---|
| | Ia | Ib | Ic | Id | Ie | If | Ig | Ii | Ij |
| $K_{obs}$ | 0.466 | 0.663 | 0.196 | 0.159 | 0.165 | 0.067 | 0.796 | 0.126 | 0.0894 |
| $k_{rel}$ | 6.93 | 9.86 | 2.93 | 2.38 | 2.45 | 1.0 | 11.8 | 1.88 | 1.33 |

Data correspond to the reaction rates measured for 19F-fluorination of the precursors.

TABLE 3

Summary of stability study

| | | \multicolumn{8}{c}{Solid (%)} | | | | | | | |
| | | 1 week | | 2 week | | 3 week | | 4 week | |
| Compounds | Start | 0° C. | −20° C. | 0° C. | −20° C. | 0° C. | −20° C. | 0° C. | −20° C. |
|---|---|---|---|---|---|---|---|---|---|
| Ia | 99.4 | 99.5 | 99.4 | 99.3 | 99.2 | 99.1 | 99.0 | 98.7 | 98.4 |
| Ib | 96.7 | 96.5 | 96.6 | 94.6 | 94.8 | 95.0 | 93.7 | 91.3 | 94.3 |
| Ic | 98.8 | 98.6 | 98.6 | 98.6 | 98.7 | 98.6 | 96.9 | 98.4 | 98.0 |
| Id | 99.8 | 99.8 | 99.8 | ND | ND | 99.8 | 99.8 | 99.8 | 99.8 |
| Ie | 99.1 | 99.0 | 98.9 | 99.0 | 99.0 | 99.0 | 98.6 | 98.6 | 97.9 |
| If | 90.5 | 89.5 | 89.6 | 89.0 | 88.5 | 89.0 | 88.3 | 89.0 | 87.0 |
| Ig | 97.9 | 97.9 | 98.0 | 98.0 | 98.1 | 97.9 | 97.9 | 97.8 | 97.5 |
| Ih | 97.6 | 94.4 | 94.6 | 95.0 | 94.8 | 93.1 | 93.1 | 93.4 | 92.8 |
| Ii | 97.2 | 89.5 | 89.6 | 97.0 | 97.0 | 96.7 | 95.6 | 95.9 | 93.2 |
| Ij | 94.8 | 97.0 | 97.2 | 97.1 | 97.0 | 96.8 | 96.0 | 96.3 | 96.6 |

ND: not determined

Preparation of Intermediates II

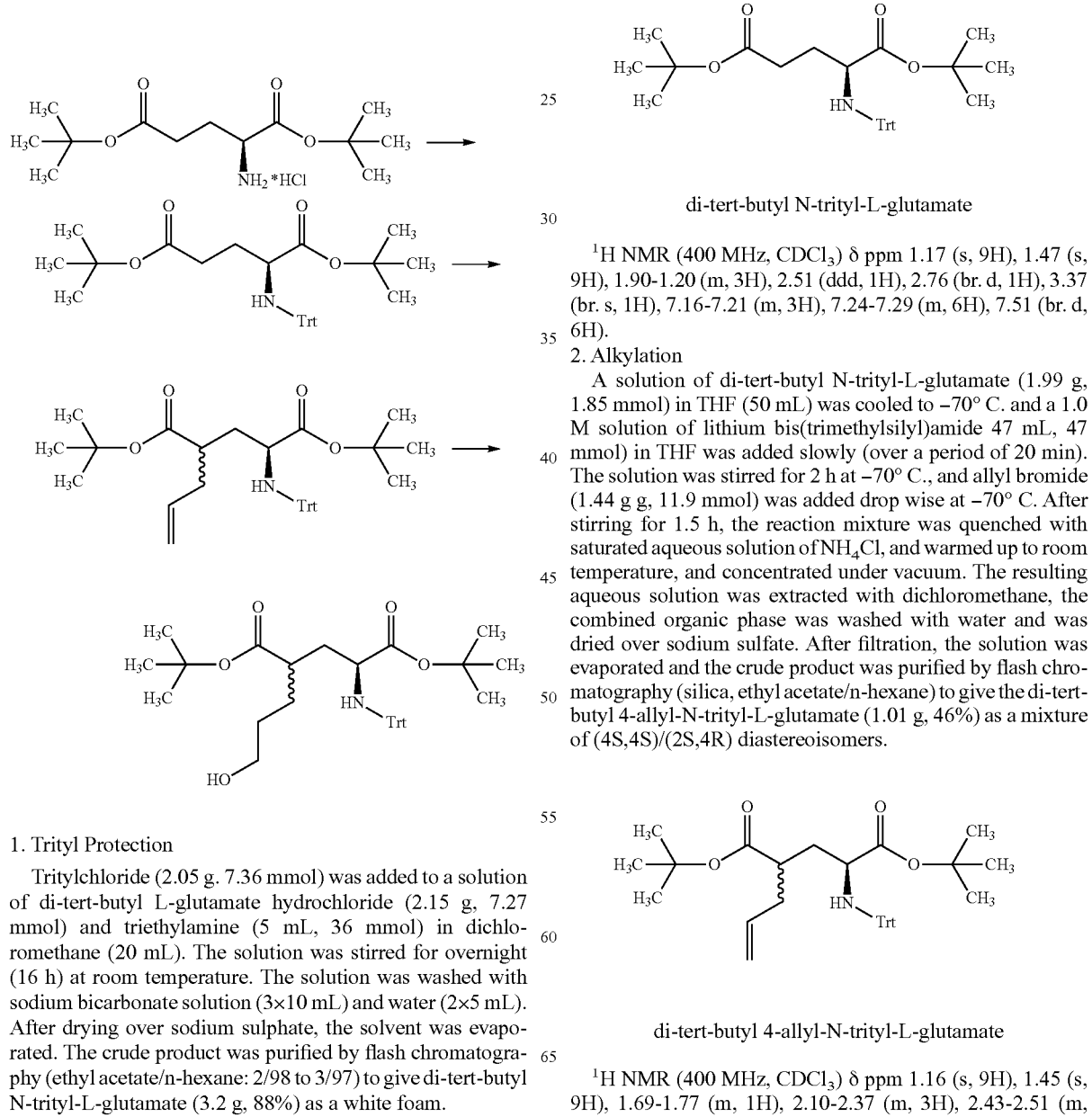

di-tert-butyl N-trityl-L-glutamate $^1$H NMR (400 MHz, CDCl$_3$) δ ppm 1.17 (s, 9H), 1.47 (s, 9H), 1.90-1.20 (m, 3H), 2.51 (ddd, 1H), 2.76 (br. d, 1H), 3.37 (br. s, 1H), 7.16-7.21 (m, 3H), 7.24-7.29 (m, 6H), 7.51 (br. d, 6H).

2. Alkylation

A solution of di-tert-butyl N-trityl-L-glutamate (1.99 g, 1.85 mmol) in THF (50 mL) was cooled to −70° C. and a 1.0 M solution of lithium bis(trimethylsilyl)amide 47 mL, 47 mmol) in THF was added slowly (over a period of 20 min). The solution was stirred for 2 h at −70° C., and allyl bromide (1.44 g g, 11.9 mmol) was added drop wise at −70° C. After stirring for 1.5 h, the reaction mixture was quenched with saturated aqueous solution of NH$_4$Cl, and warmed up to room temperature, and concentrated under vacuum. The resulting aqueous solution was extracted with dichloromethane, the combined organic phase was washed with water and was dried over sodium sulfate. After filtration, the solution was evaporated and the crude product was purified by flash chromatography (silica, ethyl acetate/n-hexane) to give the di-tert-butyl 4-allyl-N-trityl-L-glutamate (1.01 g, 46%) as a mixture of (4S,4S)/(2S,4R) diastereoisomers.

di-tert-butyl 4-allyl-N-trityl-L-glutamate

1. Trityl Protection

Tritylchloride (2.05 g. 7.36 mmol) was added to a solution of di-tert-butyl L-glutamate hydrochloride (2.15 g, 7.27 mmol) and triethylamine (5 mL, 36 mmol) in dichloromethane (20 mL). The solution was stirred for overnight (16 h) at room temperature. The solution was washed with sodium bicarbonate solution (3×10 mL) and water (2×5 mL). After drying over sodium sulphate, the solvent was evaporated. The crude product was purified by flash chromatography (ethyl acetate/n-hexane: 2/98 to 3/97) to give di-tert-butyl N-trityl-L-glutamate (3.2 g, 88%) as a white foam.

$^1$H NMR (400 MHz, CDCl$_3$) δ ppm 1.16 (s, 9H), 1.45 (s, 9H), 1.69-1.77 (m, 1H), 2.10-2.37 (m, 3H), 2.43-2.51 (m, 1H), 2.74 (br. d, 1H), 3.26-3.33 (m, 1H), 4.96-5.06 (m, 2H), 5.63-5.76 (m, 1H), 7.14-7.18 (m, 3H), 7.21-7.27 (m, 6H), 7.45-7.51 (m, 6H).

MS (ES+) $C_{35}H_{43}NO_4$: m/z 541 [M]$^+$.

Methods to separate diastereoisomers are known to person skilled in the art (e.g. chromatography methods) allowing an access to pure the isomers (2S/2R) and (2S/4S) that can be further converted to isomerical pure compounds similar as described in the subsequent steps below.

3. Hydroboration

Borane tetrahydrofuran complex (1M, 2.8 mL, 2.8 mmol) was added drop wise to a solution of di-tert-butyl 4-allyl-N-trityl-L-glutamate (1.00 g, 1.85 mmol) in THF (10 mL) at 0° C. The resulting mixture was stirred for 2 h at 0° C. and for 16 h at room temperature. The solution was cooled to 0° C. NaOH (1M, 3 mL) and $H_2O_2$ (30% in water, 3 mL) were added drop wise. The mixture was stirred at 0° C. for 1 h. Water (5 mL) was added and the mixture was concentrated under reduced pressure. The aqueous residue was extracted with ethyl acetate. The combined organic fraction was washed with brine, dried over sodium sulfate, filtrated and concentrated. The crude product was purified by flash chromatography (silica, ethyl acetate/hexane) to afford di-tert-butyl 4-(3-hydroxypropyl)-N-trityl-L-glutamate (0.46 g, 44%) as a mixture of (4S,4S)/(2S,4R) diastereoisomers.

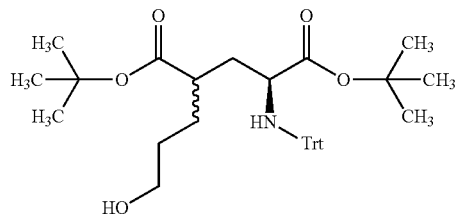

di-tert-butyl 4-(3-hydroxypropyl)-N-trityl-L-glutamate $^1$H NMR (400 MHz, CDCl$_3$) δ ppm 1.16 (s, 9H), 1.47 (s, 9H), 1.48-1.78 (m, 5H), 2.06-2.20 (m, 1H), 2.35-2.45 (m, 1H), 2.70-2.82 (m, 1H), 3.23-3.34 (m, 1H), 3.55-3.67 (m, 2H), 7.12-7.20 (m, 3H), 7.21-7.30 (m, 6H), 7.45-7.53 (m, 6H).

MS (ES+) $C_{35}H_{45}NO_5$: m/z 560 [M]$^+$.

Methods to separate diastereoisomers are known to person skilled in the art (e.g. chromatography methods) allowing an access to pure the isomers (2S/2R) and (2S/4S) that can be further converted to isomerical pure compounds similar as described in the subsequent steps below.

Example Compounds of the Invention (Precursor Compounds) II

Di-tert-butyl (4S)-4-{3-[(2-naphthylsulfonyl)oxy]propyl}-N-trityl-L-glutamate (Id) and Di-tert-butyl (4R)-4-{3-[(2-naphthylsulfonyl)oxy]propyl}-N-trityl-L-glutamate (Ik)

At 0° C. triethylamine (0.68 mL, 4.90 mmol) and naphthalene-2-sulfonyl chloride (0.370 g, 1.63 mmol) were added to a solution of di-tert-butyl 4-(3-hydroxypropyl)-N-trityl-L-glutamate (0.457 g, 0.816 mmol) in dichloromethane (10 mL). The resulting mixture was stirred at 0° C. for 2 h and for 16 h at room temperature. The solution was concentrated and the crude product was purified by flash chromatography (silica, ethyl acetate/hexane) to afford di-tert-butyl 4-{3-[(2-naphthylsulfonyl)oxy]propyl}-N-trityl-L-glutamate (0.479 mg, 78%) as a mixture of (4S,4S)/(2S,4R) diastereoisomers. The isomers were separated by chiral HPLC (Chiralpak IC 5 μm 250×30 mm, ethanol/methanol 1:1, 30 mL/min):

di-tert-butyl (4S)-4-{3-[(2-naphthylsulfonyl)oxy]propyl}-N-trityl-L-glutamate (Id): 80 mg, 13%, di-tert-butyl (4R)-4-{3-[(2-naphthylsulfonyl)oxy]propyl}-N-trityl-L-glutamate (Ik): 323 mg, 53%.

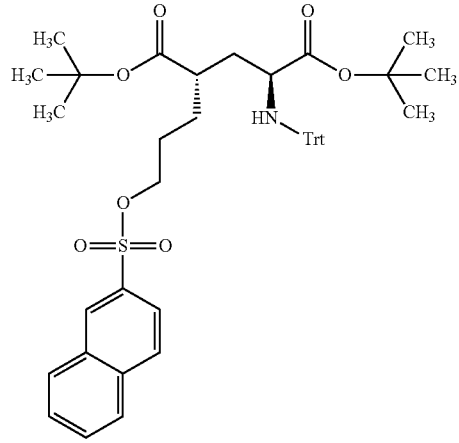

di-tert-butyl (4S)-4-{3-[(2-naphthylsulfonyl)oxy]propyl}-N-trityl-L-glutamate (Id)

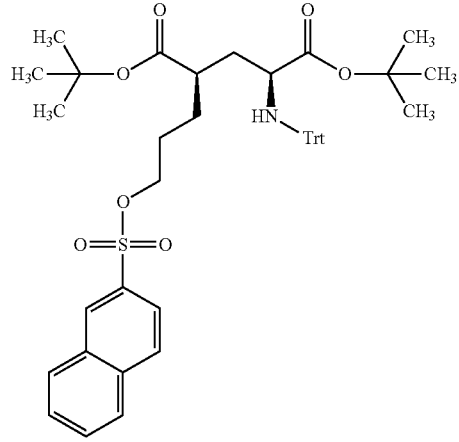

di-tert-butyl (4R)-4-{3-[(2-naphthylsulfonyl)oxy]propyl}-N-trityl-L-glutamate (Ik)

Id:
$^1$H NMR (400 MHz, CDCl$_3$) δ 1.12 (s, 9H), 1.27 (s, 9H), 1.50-1.70 (m, 5H), 2.00-2.10 (m, 1H), 2.22-2.32 (m, 1H), 2.74 (d, J=8.8 Hz, 1H), 3.14-3.24 (m, 1H), 4.04 (t, J=6.4 Hz, 2H), 7.10-7.16 (m, 3H), 7.18-7.24 (m, 6H), 7.40-7.46 (m, 6H), 7.60-7.72 (m, 2H), 7.85 (dd, J=1.6, 8.0 Hz, 1H), 7.93 (d, J=8.0 Hz, 1H), 7.96-8.02 (m, 2H), 8.48 (d, J=1.2 Hz, 1H).

MS (ES+) $C_{45}H_{51}NO_7S$: m/z 750 [M]$^+$.

Ik:
$^1$H NMR (400 MHz, CDCl$_3$) δ 1.14 (s, 9H), 1.41 (s, 9H), 1.43-1.52 (m, 3H), 1.55-1.64 (m, 2H), 2.10 (ddd, 1H), 2.31-2.37 (m, 1H), 2.71 (br. d, 1H), 3.22 (td, 1H), 4.03 (t, 2H), 7.16 (d, 3H), 7.20-7.25 (m, 6H), 7.45-7.49 (m, 6H), 7.65 (ddd, 1H), 7.69 (ddd, 1H), 7.84 (dd, 1H), 7.93 (d, 1H), 7.76 (d, 2H), 7.99 (dd, 1H), 8.49 (d, 1H).

MS (ES$^+$) $C_{45}H_{51}NO_7S$: m/z 750 [M]$^+$.

Di-tert-butyl (4S)-4-{3-{[(4-methylphenyl)sulfonyl]propyl}-N-trityl-L-glutamate (Im) and Di-tert-butyl (4R)-4-{3-{[(4-methylphenyl)sulfonyl)oxy]propyl}-N-trityl-L-glutamate (In)

At 0° C. triethylamine (0.31 mL, 2.2 mmol) and 4-methylbenzenesulfonyl chloride (0.141 g, 0.74 mmol) were added to a solution of di-tert-butyl 4-(3-hydroxypropyl)-N-trityl-L-glutamate (0.239 g, 0.427 mmol) in dichloromethane (10 mL). The resulting mixture was stirred at 0° C. for 2 h and for 16 h at room temperature. The solution was concentrated and the crude product was purified by flash chromatography (silica, ethyl acetate/hexane) to afford di-tert-butyl 4-{3-{[(4-methylphenyl)sulfonyl)oxy]propyl}-N-trityl-L-glutamate (0.255 mg, 67%) as a mixture of (4S,4S)/(2S,4R) diastereoisomers. The isomers were separated by chiral HPLC (Chiralpak AD-H 5 μm 250×20 mm, hexane/2-propanol 9:1, 25 mL/min):

di-tert-butyl (4S)-4-{3-{[(4-methylphenyl)sulfonyl]propyl}-N-trityl-L-glutamate (Im): 34 mg (11%)

di-tert-butyl (4R)-4-{3-{[(4-methylphenyl)sulfonyl)oxy]propyl}-N-trityl-L-glutamate (In): 127 mg (42%).

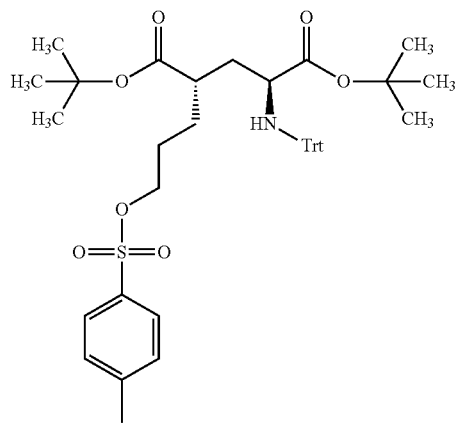

di-tert-butyl (4S)-4-{3-{[(4-methylphenyl)sulfonyl]propyl}-N-trityl-L-glutamate (Im)

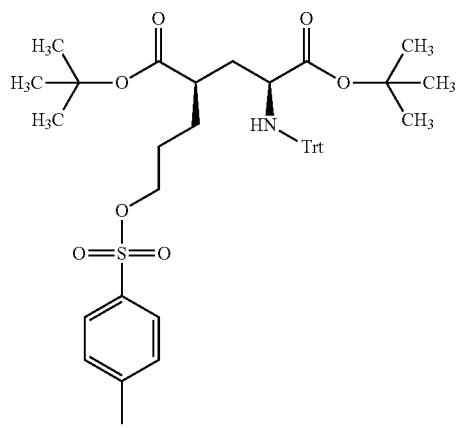

di-tert-butyl (4R)-4-{3-{[(4-methylphenyl)sulfonyl)oxy]propyl}-N-trityl-L-glutamate (In)

Im
$^1$H NMR (400 MHz, CDCl$_3$) δ 1.14 (s, 9H), 1.30 (s, 9H), 1.45-1.68 (m, 5H), 2.03-2.15 (m, 1H), 2.22-2.31 (m, 1H), 2.44 (s, 3H), 2.75 (m$_c$, 1H), 3.21 (dd, 1H), 4.00 (t, 2H), 7.12-7.18 (m, 3H), 7.21-7.28 (m, 6H), 7.33 (d, 2H), 7.41-7.47 (m, 6H), 7.78 (d, 2H).

In
$^1$H NMR (400 MHz, CDCl$_3$) δ 1.15 (s, 9H), 1.42 (s, 9H), 1.48-1.65 (m, 5H), 2.10 (ddd, 1H), 2.34 (dt, 1H), 2.44 (s, 3H), 2.71 (br. s, 1H), 3.23 (br. s, 1H), 3.95 (t, 2H), 7.13-7.18 (m, 3H), 7.21-7.29 (m, 6H), 7.32 (d, 2H), 7.43-7.48 (m, 6H), 7.76 (d, 2H).

$^{18}$F-Fluorination of Example Compounds II

Radiolabeling of di-tert-butyl (4R)-4-{3-{[(4-methylphenyl)sulfonyl)oxy]propyl}-N-trityl-L-glutamate (In)

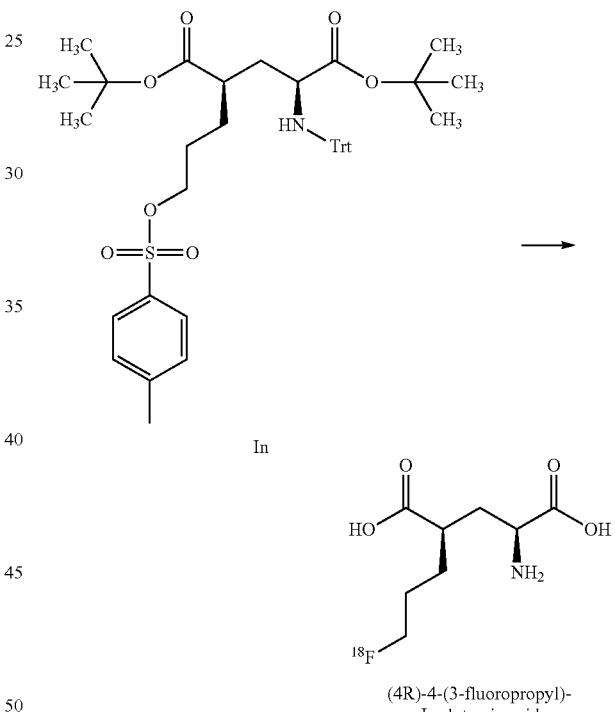

(4R)-4-(3-fluoropropyl)-L-glutamic acid

The radiolabeling was performed on a GE Tracerlab MX synthesizer. [$^{18}$F]Fluoride (968 MBq) was trapped an anion exchange cartridge (QMA light, Waters). The activity was eluted with a solution of 5 mg kryptofix and 1 mg potassium carbonate in 600 μL acetonitrile/water (1:1). The mixture was dried by heating under gentle nitrogen stream and vacuum. Drying was repeated after addition of acetonitrile. 5.9 mg di-tert-butyl (4R)-4-{3-{[(4-methylphenyl)sulfonyl)oxy]propyl}-N-trityl-L-glutamate (In) in 1.5 mL acetonitrile were added and the mixture was heated at 120° C. for 5 min. After addition of 2 mL HCl (2M), the mixture was heated for 5 min at 130° C. 1.5 mL NaOH (4M) were added and the mixture was heated for 5 min at 70° C. The crude product was diluted with 2 mL HCl (2M) and water (up to 30 mL) and passed through two MCX cartridges (MCX plus, Waters). The cartridges were washed with water (30 mL) and the radiolabeled product was eluted from the MCX cartridges through a Hypercarb cartridge (Hypercarb 500 mg, Thermo Scientific) with 15 mL phosphate buffer (7 g Na$_2$HPO$_4$ 2 H$_2$O; 6 g NaCl in 1 l H$_2$O) into the product vial to obtain 381 MBq (34% d.c.) (4R)-4-(3-fluoropropyl)-L-glutamic acid. The radiochemical purity was determined to be >96% by radio-HPLC (Luna 5µ C18(2); 250*4.6 mm; 5µ; Phenomenex; 12-100% acetonitrile in 0.01M Na$_2$HPO$_4$; pre-column derivatization with Fluoraldehyde, o-Phthalaldehyde Reagent Solution; Thermo Scientific).

Radiolabeling of di-tert-butyl (4S)-4-{3-[(2-naphthylsulfonyl)oxy]propyl}-N-trityl-L-glutamate (Id)

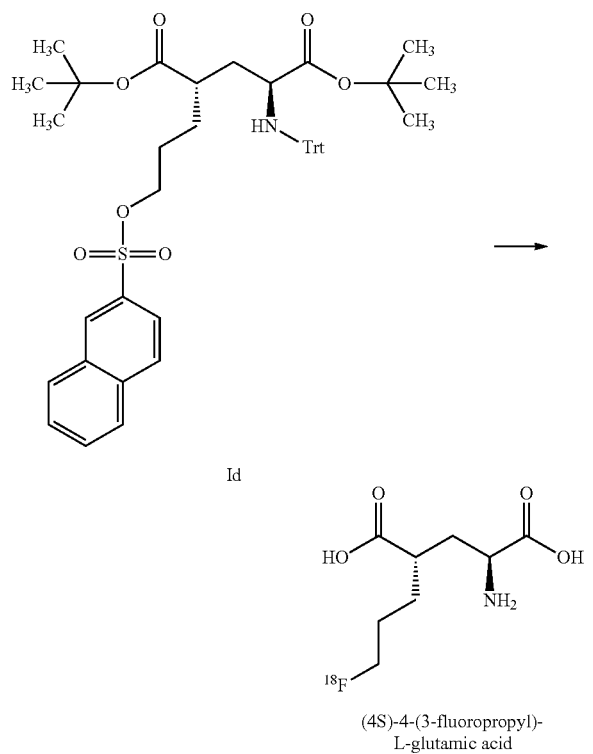

Id (4S)-4-(3-fluoropropyl)-L-glutamic acid

The radiolabeling was performed on a GE Tracerlab MX synthesizer. [$^{18}$F]Fluoride (2915 MBq) was trapped an anion exchange cartridge (QMA light, Waters). The activity was eluted with a solution of 3 mg kryptofix and 0.6 mg potassium carbonate in 800 µL acetonitrile/water (1:1). The mixture was dried by heating under gentle nitrogen stream and vacuum. Drying was repeated after addition of acetonitrile. 6 mg di-tert-butyl (4S)-4-{3-[(2-naphthylsulfonyl)oxy]propyl}-N-trityl-L-glutamate (Id) in 1.5 mL acetonitrile were added and the mixture was heated at 130° C. for 5 min. After addition of 2 mL HCl (2M), the mixture was heated for 10 min at 120° C. The crude product was diluted with water (up to 30 mL) and passed through two MCX cartridges (MCX plus, Waters). The cartridges were washed with water (30 mL) and the radiolabeled product was eluted from the MCX cartridges through a Hypercarb cartridge (Hypercarb 500 mg, Thermo Scientific) with 10 mL phosphate buffer (7 g Na$_2$HPO$_4$ 2 H$_2$O; 6 g NaCl in 1 l H$_2$O) into the product vial to obtain 1168 MBq (40% n.d.c.) (4S)-4-(3-fluoropropyl)-L-glutamic acid. The radiochemical purity was determined to be >96% by radio-HPLC >95% by radio-HPLC (Advanced Chromatography Technologies ACE 5 C18 250×4.6 mm; 2-100% B in 0.04M Na$_2$HPO$_4$; B: 45% acetonitrile, 45% methanol, 10% water; pre-column derivatization with o-Phthalaldehyde Reagent Solution; Agilent).

Radiolabeling of di-tert-butyl (4R)-4-{3-[(2-naphthylsulfonyl)oxy]propyl}-N-trityl-L-glutamate (Ik)

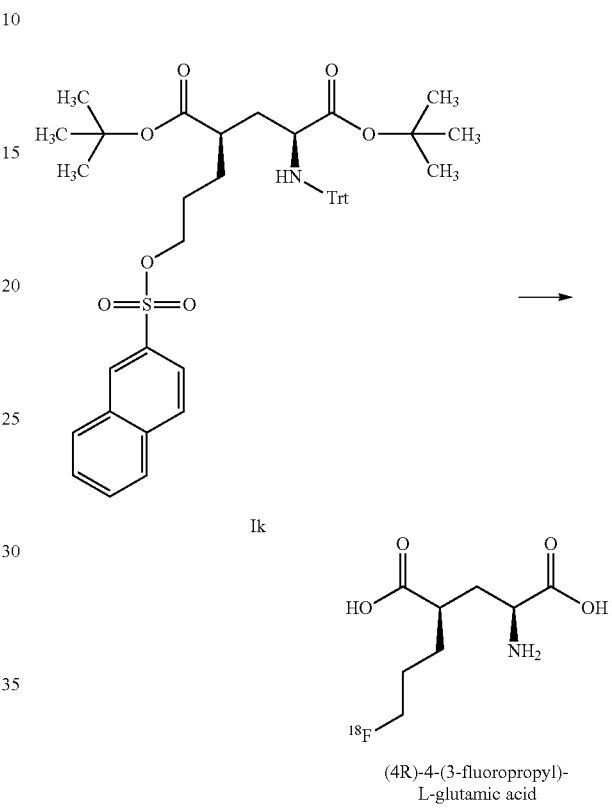

Ik (4R)-4-(3-fluoropropyl)-L-glutamic acid

The radiolabeling was performed on a GE Tracerlab MX synthesizer. [$^{18}$F]Fluoride (9400 MBq) was trapped an anion exchange cartridge (QMA light, Waters). The activity was eluted with a solution of 3 mg kryptofix and 0.6 mg potassium carbonate in 800 µL acetonitrile/water (1:1). The mixture was dried by heating under gentle nitrogen stream and vacuum. Drying was repeated after addition of acetonitrile. 6 mg di-tert-butyl (4R)-4-{3-[(2-naphthylsulfonyl)oxy]propyl}-N-trityl-L-glutamate (Ik) in 1.5 mL acetonitrile were added and the mixture was heated at 130° C. for 5 min. After addition of 2 mL HCl (2M), the mixture was heated for 10 min at 120° C. The crude product was diluted with water (up to 30 mL) and passed through two MCX cartridges (MCX plus, Waters). The cartridges were washed with water (30 mL) and the radiolabeled product was eluted from the MCX cartridges through a Hypercarb cartridge (Hypercarb 500 mg, Thermo Scientific) with 10 mL phosphate buffer (7 g Na$_2$HPO$_4$ 2 H$_2$O; 6 g NaCl in 1 l H$_2$O) into the product vial to obtain 5100 MBq (54% n.d.c.) (4R)-4-(3-fluoropropyl)-L-glutamic acid. The radiochemical purity was determined to be >96% by radio-HPLC >95% by radio-HPLC (Advanced Chromatography Technologies ACE 5 C18 250×4.6 mm; 2-100% B in 0.04M Na$_2$HPO$_4$; B: 45% acetonitrile, 45% methanol, 10% water; pre-column derivatization with o-Phthalaldehyde Reagent Solution; Agilent).

The invention claimed is:

1. A compound of the formula I

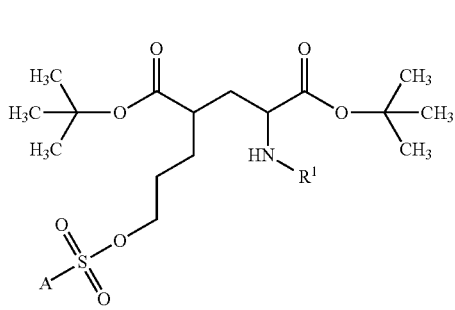

Formula I wherein
R¹ is triphenylmethyl,
A is selected from the group consisting of:
  a) Monocyclic aryl,
  b) Bicyclic aryl,
  c) Biaryl,
  d) Monocyclic heteroaryl, and
  e) Bicyclic heteroaryl
optionally, A is bearing one or more substituents selected from the group consisting of:
  a) Halogen,
  b) Nitro,
  c) Alkyl,
  d) Trifluoromethyl, and
  e) Z,
wherein Z is

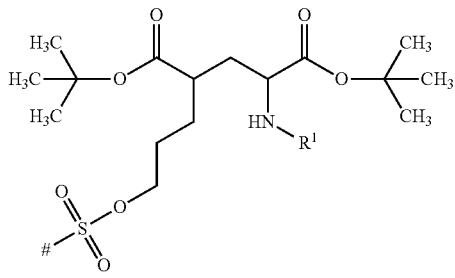

where R¹ is triphenylmethyl, and
# indicates the position of the bond to A, or
a single isomer, tautomer, diastereomer, enantiomer or stereoisomer thereof, or mixtures thereof, or a suitable salt thereof.

2. The compound according to claim 1 wherein
A is selected from the group consisting of:
  a) phenyl,
  b) biphenyl,
  c) naphthyl, and
  d) quinolinyl,
optionally, A is bearing one or more substituents selected from the group consisting of:
  a) Halogen,
  b) Nitro,
  c) C₁—C₃ alkyl,
  d) Trifluoromethyl, and
  e) Z.

3. The compound according to claim 1 with (2S,4S)-configuration of formula 1a

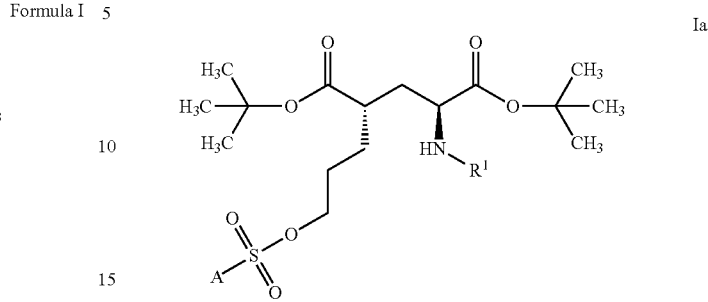

Ia

R¹ and A are as defined in claim 1.

4. Compound according to claim 1 selected from the list below

Di-tert-butyl (4S)-4-(3-{[(4-nitrophenyl)sulfonyl]oxy}propyl)-N-trityl-L-glutamate

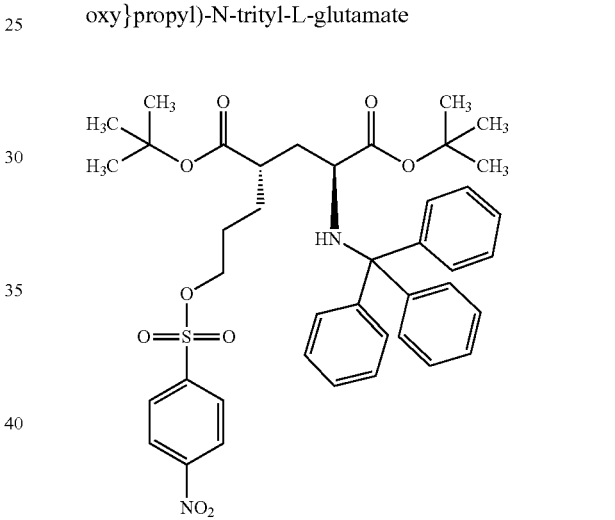

Di-tert-butyl (4S)-4-(3-{[(3-nitrophenyl)sulfonyl]oxy}propyl)-N-trityl-L-glutamate

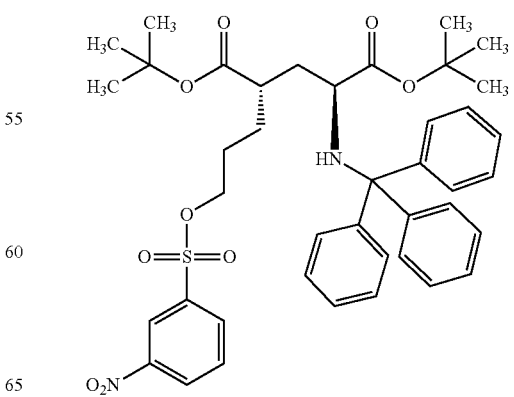

Di-tert-butyl) (4S)-4-{3-[biphenyl-4-ysulfonyl)oxy]propyl}-N-trityl-L-glutamate

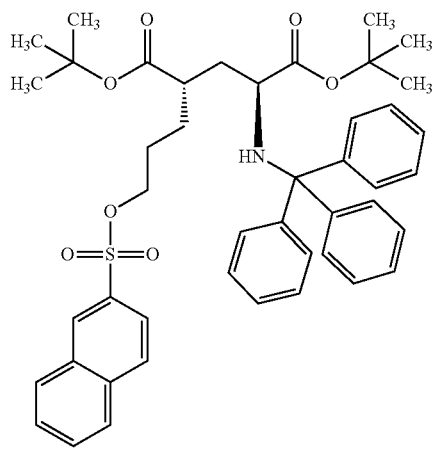 [SMILES: CC(C)(C)OC(=O)[C@@H](CCCOS(=O)(=O)c1ccc2ccccc2c1)C[C@H](NC(c1ccccc1)(c1ccccc1)c1ccccc1)C(=O)OC(C)(C)C]

Di-tert-butyl (4S)-4-{3-[(2-naphthylsulfonyl)oxy]propyl}-N-trityl-L-glutamate

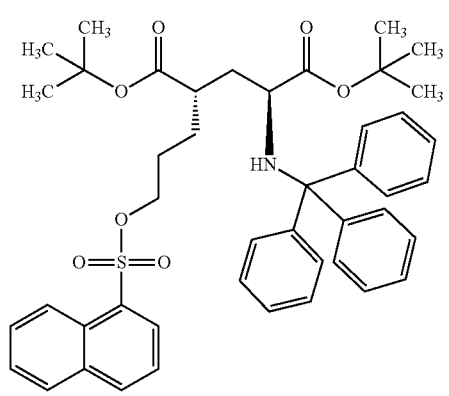 [SMILES: CC(C)(C)OC(=O)[C@@H](CCCOS(=O)(=O)c1cccc2ccccc12)C[C@H](NC(c1ccccc1)(c1ccccc1)c1ccccc1)C(=O)OC(C)(C)C]

Di-tert-butyl (4S)-4-{3-[(1-naphthylsulfonyl)oxy]propyl}-N-trityl-L-glutamate

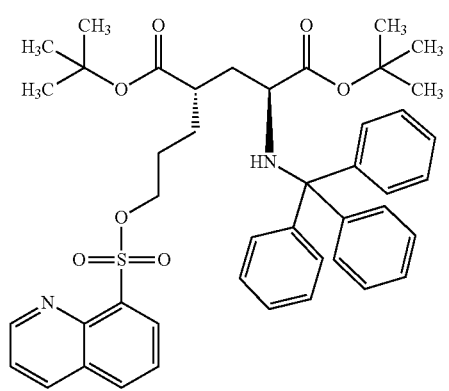 [SMILES: CC(C)(C)OC(=O)[C@@H](CCCOS(=O)(=O)c1cccc2cccnc12)C[C@H](NC(c1ccccc1)(c1ccccc1)c1ccccc1)C(=O)OC(C)(C)C]

Di-tert-butyl (4S)-4-(3-{[(2,4,6-trichlorophenyl)sulfonyl]oxy}propyl)-N-trityl-L-glutamate

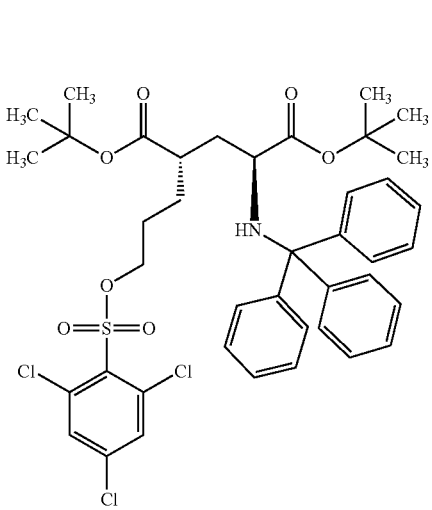 [SMILES: CC(C)(C)OC(=O)[C@@H](CCCOS(=O)(=O)c1c(Cl)cc(Cl)cc1Cl)C[C@H](NC(c1ccccc1)(c1ccccc1)c1ccccc1)C(=O)OC(C)(C)C]

Tetra-tert-butyl (2S,4S,2'S,4'S)-2,2'-[biphenyl-4,4'-diylbis(sulfonyloxypropane-3,1-diyl)]bis[4-(tritylamino)pentanedioate]

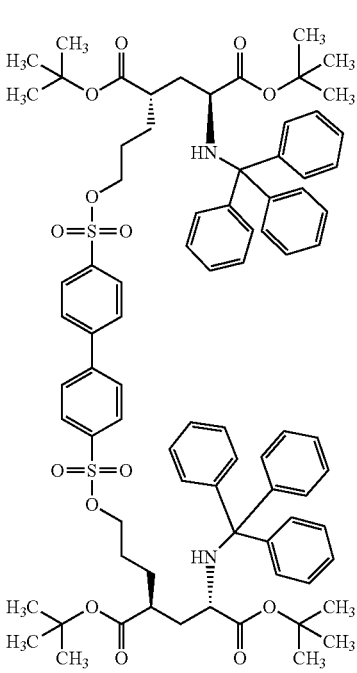 [SMILES: CC(C)(C)OC(=O)[C@@H](CCCOS(=O)(=O)c1ccc(-c2ccc(S(=O)(=O)OCCC[C@@H](C[C@H](NC(c3ccccc3)(c3ccccc3)c3ccccc3)C(=O)OC(C)(C)C)C(=O)OC(C)(C)C)cc2)cc1)C[C@H](NC(c1ccccc1)(c1ccccc1)c1ccccc1)C(=O)OC(C)(C)C]

Di-tert-butyl (4S)-4-(3-{[(7-nitro-1-naphthyl)sulfonyl]oxy}propyl)-N-trityl-L-glutamate

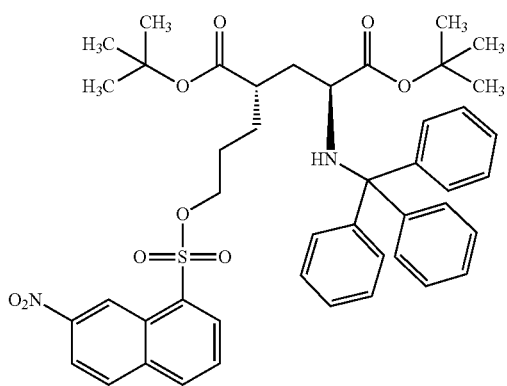 [SMILES: CC(C)(C)OC(=O)[C@@H](CCCOS(=O)(=O)c1cccc2ccc([N+](=O)[O-])cc12)C[C@H](NC(c1ccccc1)(c1ccccc1)c1ccccc1)C(=O)OC(C)(C)C]

Di-tert-butyl (4S)-4-[3-({[4-nitro-3-(trifluoromethyl)phenyl]sulfonyl}oxy)propyl]-N-trityl-L-glutamate

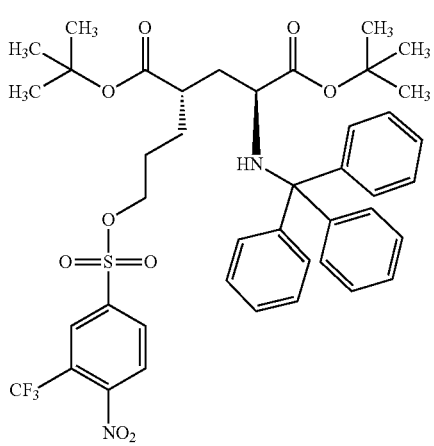 [SMILES: CC(C)(C)OC(=O)[C@@H](CCCOS(=O)(=O)c1ccc([N+](=O)[O-])c(C(F)(F)F)c1)C[C@H](NC(c1ccccc1)(c1ccccc1)c1ccccc1)C(=O)OC(C)(C)C]

di-tert-butyl (4S)-4-(3-{[(4-methylphenyl)sulfonyl]oxy}propyl)-N-trityl-L-glutamate

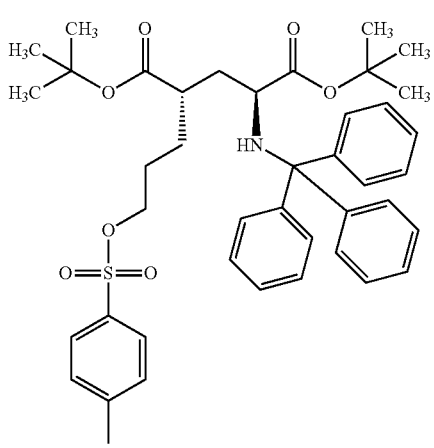 [SMILES: Cc1ccc(S(=O)(=O)OCCC[C@@H](C[C@H](NC(c2ccccc2)(c2ccccc2)c2ccccc2)C(=O)OC(C)(C)C)C(=O)OC(C)(C)C)cc1]

di-tert-butyl (4R)-4-{3-[(2-naphthylsulfonyl)oxy]propyl}-N-trityl-L-glutamate

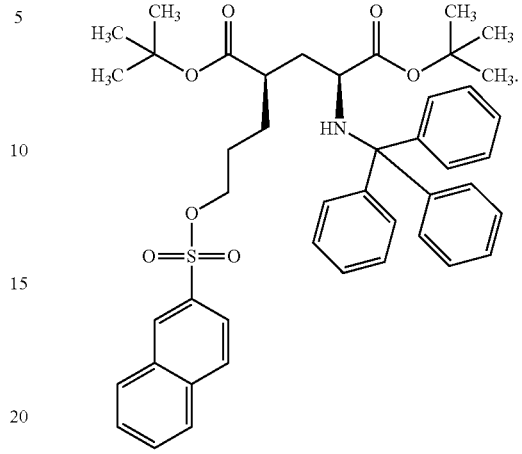

5. A compound of Formula I according to claim 1 in the solid form.

6. A method for obtaining compounds of formula I comprising the step:

Sulfonylation of a compound of Formula II with a sulfonylhalide or sulfonyl anhydride having a suitable substituent A,

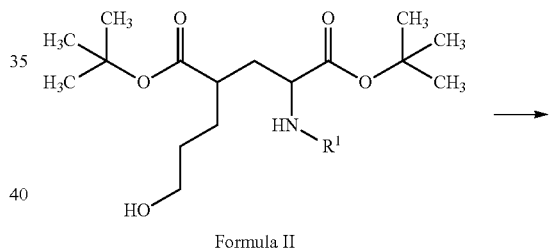

Formula II

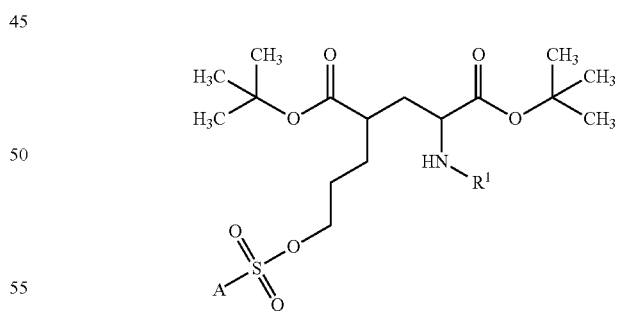

Formula I wherein $R^1$ is triphenylmethyl,

A is selected from the group:
  a) Monocyclic aryl,
  b) Bicyclic aryl,
  c) Biaryl,
  d) Monocyclic heteroaryl, and
  e) Bicyclic heteroaryl optionally, A is bearing one or more substituents selected from the group comprising:
  a) Halogen,
  b) Nitro,
  c) Alkyl,
  d) Trifluoromethyl, and
  e) Z,
wherein Z is

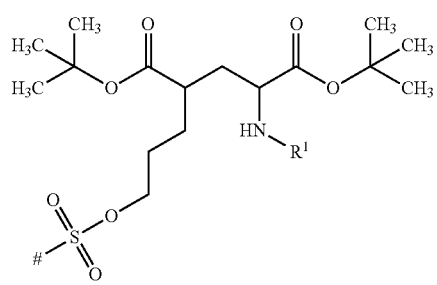

$R^1$ is triphenylmethyl (Trityl), and
# indicates the position of the bond to A.

7. The method according to claim 6 for obtaining a compound with (2S,4S)-configuration (of formula Ia wherein the compound of formula II is a compound of the formula IIa:

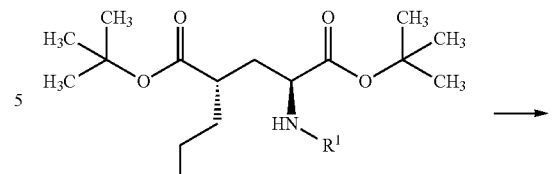

Formula IIa

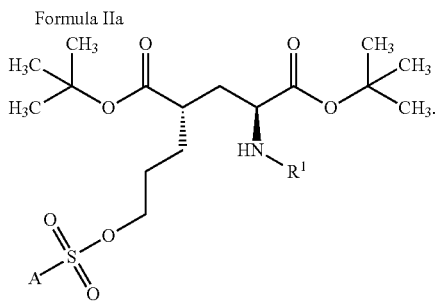

Formula Ia

8. A composition comprising a compound of formula I.

9. A kit comprising one vial or more than one vial comprising a predetermined quantity of compounds of Formula I.

* * * * *